(12) United States Patent
Gittings et al.

(10) Patent No.: US 6,517,558 B2
(45) Date of Patent: Feb. 11, 2003

(54) METHODS AND DEVICES FOR FORMING VASCULAR ANASTOMOSES

(75) Inventors: Darin C. Gittings, Sunnyvale; Wally S. Buch, Atherton; Alan R. Rapacki, Redwood City, all of CA (US)

(73) Assignee: Ventrica, Inc., Fremont, CA (US)

( * ) Notice: Subject to any disclaimer, the term of this patent is extended or adjusted under 35 U.S.C. 154(b) by 0 days.

(21) Appl. No.: 09/776,230

(22) Filed: Feb. 1, 2001

(65) Prior Publication Data

US 2001/0004699 A1 Jun. 21, 2001

Related U.S. Application Data

(63) Continuation of application No. 09/232,103, filed on Jan. 15, 1999, now abandoned.

(51) Int. Cl.[7] ............................................... A61B 17/02
(52) U.S. Cl. ....................................................... 606/153
(58) Field of Search ................................. 606/151, 153, 606/154, 108

(56) References Cited

U.S. PATENT DOCUMENTS

| | | |
|---|---|---|
| 2,127,903 A | 8/1938 | Bowen |
| 3,042,021 A | 7/1962 | Read |
| 4,368,736 A | 1/1983 | Kaster |
| 4,769,029 A | 9/1988 | Patel |
| 5,054,484 A | 10/1991 | Hebeler, Jr. |
| 5,429,144 A * | 7/1995 | Wilk ........................... 128/898 |
| 5,443,497 A | 8/1995 | Venbrux |
| 5,466,242 A | 11/1995 | Mori |
| 5,591,226 A | 1/1997 | Trerotola et al. |
| 5,653,743 A | 8/1997 | Martin |
| 5,702,412 A | 12/1997 | Popov et al. |
| 5,755,682 A | 5/1998 | Knudson et al. |
| 5,755,775 A * | 5/1998 | Trerotola et al. .......... 623/1.11 |
| 5,755,778 A | 5/1998 | Kleshinski |
| 5,836,316 A | 11/1998 | Plaia et al. |

(List continued on next page.)

FOREIGN PATENT DOCUMENTS

| | | |
|---|---|---|
| WO | WO 88/06865 | 9/1988 |
| WO | WO 96/22745 | 8/1996 |
| WO | WO 97/12555 | 4/1997 |
| WO | WO 98/19630 | 5/1998 |
| WO | WO 98/38939 | 9/1998 |
| WO | WO 98/38941 | 9/1998 |
| WO | WO 98/38942 | 9/1998 |
| WO | WO 98/57590 | 12/1998 |
| WO | WO 98/57592 | 12/1998 |
| WO | WO 99/18887 | 4/1999 |
| WO | WO 99/63910 | 12/1999 |
| WO | WO 99/65409 | 12/1999 |
| WO | WO 00/69364 | 11/2000 |
| WO | WO 00/74579 | 12/2000 |
| WO | WO 01/39672 | 6/2001 |

OTHER PUBLICATIONS

JOMED Direction, product literature, no date.

*Primary Examiner*—Olik Chaudhuri
*Assistant Examiner*—(Vikki) Hoa B. Trinh
(74) *Attorney, Agent, or Firm*—Hoekendijk & Lynch, LLP

(57) ABSTRACT

Methods and devices for forming an anastomosis utilize a graft vessel secured to a vessel coupling that is fixed to a target vessel without using suture. The vessel coupling may be collapsed for introduction into the target vessel and then expanded to engage the vessel wall. The vessel coupling may be a stent attached to a graft vessel to form a stent-graft assembly. The anastomosis may be carried out to place the graft and target vessels in fluid communication while preserving native proximal flow through the target vessel, which may be a coronary artery. As a result, blood flowing through the coronary artery from the aorta is not blocked by the vessel coupling and thus is free to move past the site of the anastomosis.

11 Claims, 23 Drawing Sheets

U.S. PATENT DOCUMENTS

| | | |
|---|---|---|
| 5,893,369 A | 4/1999 | Lemole |
| 5,904,697 A | 5/1999 | Gifford et al. |
| 5,972,017 A | 10/1999 | Berg et al. |
| 5,989,276 A | 11/1999 | Houser et al. |
| 6,035,856 A | 3/2000 | Lafontaine et al. |
| 6,074,416 A | 6/2000 | Berg et al. |
| 6,092,526 A | 7/2000 | Lafontaine et al. |
| 6,165,185 A | 12/2000 | Shennib et al. |
| 6,176,864 B1 | 1/2001 | Chapman |
| 6,241,741 B1 * | 6/2001 | Duhaylongsod et al. .... 606/153 |
| 6,253,769 B1 | 7/2001 | Lafontaine et al. |

* cited by examiner

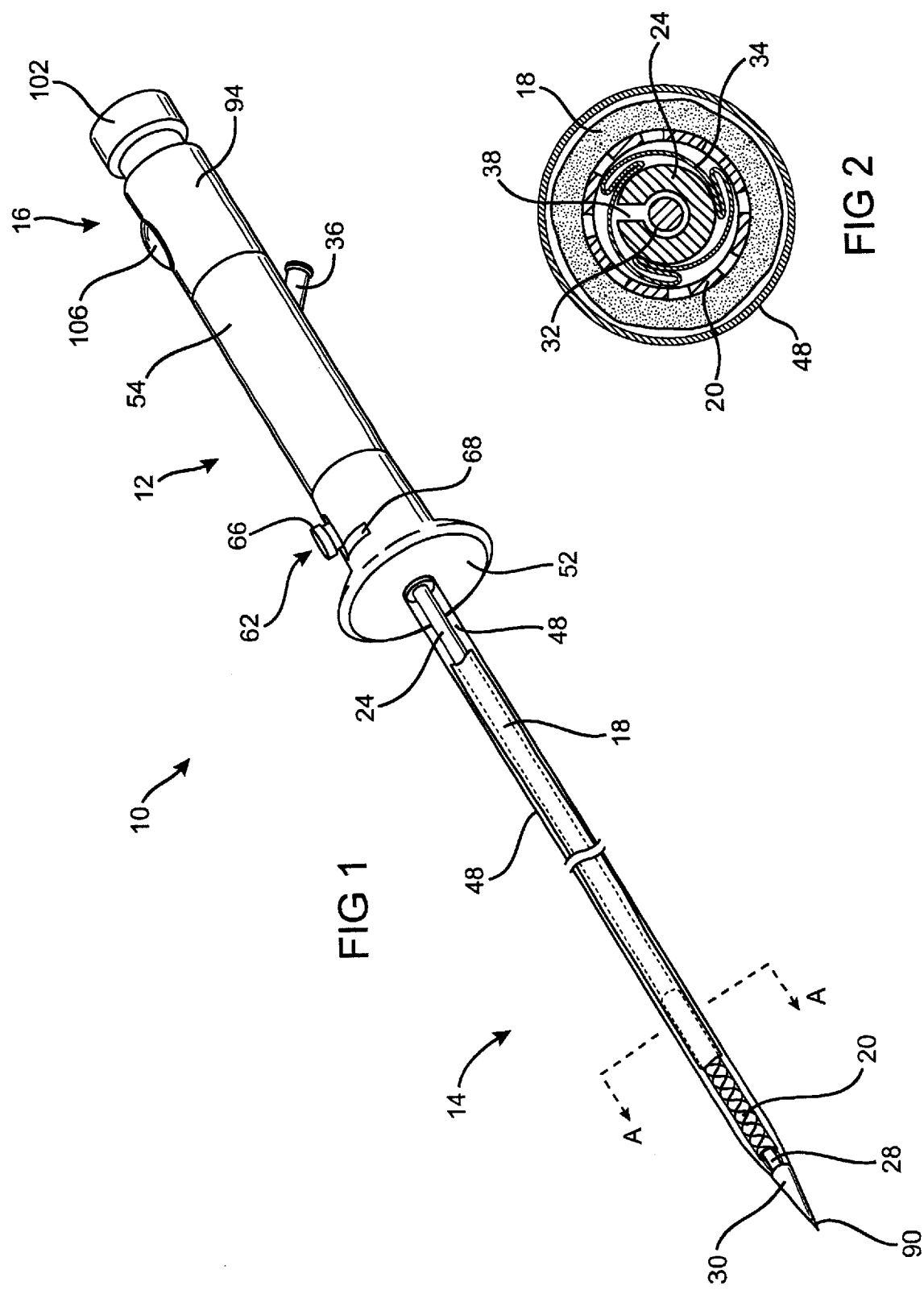

METHODS AND DEVICES FOR FORMING VASCULAR ANASTOMOSES

This application is a continuation of Ser. No. 09/232,103 filed Jan. 15, 1999 now abandoned.

BACKGROUND OF THE INVENTION

1. Field of the Invention

The invention relates to methods and devices for anastomosing a graft vessel to a target vessel, and more particularly methods and devices for forming such an anastomosis which is substantially suture-free or preserves native blood flow through the target vessel.

2. Description of Related Art

Despite the considerable advances that have been realized in cardiology and cardiovascular surgery, heart disease remains the leading cause of death throughout much of the world. Coronary artery disease, or arteriosclerosis, is the single leading cause of death in the United States today. As a result, those in the cardiovascular field continue to search for new and improved treatments.

Coronary artery disease is currently treated by interventional procedures such as percutaneous transluminal coronary angioplasty (PTCA), atherectomy and intracoronary stenting, as well as surgical procedures including coronary artery bypass grafting (CABG). The goal of these procedures is to reestablish or improve blood flow through occluded (or partially occluded) coronary arteries, which is accomplished, for example, by enlarging the blood flow lumen of the artery or by forming a bypass that allows blood to circumvent the occlusion. What procedure(s) is used typically depends on the severity and location of the blockages. When successful, these procedures restore blood flow to myocardial tissue that had not been sufficiently perfused due to the occlusion.

CABG, the most common surgical procedure to treat coronary artery disease, uses a graft vessel to deliver oxygenated blood to a coronary artery downstream of the obstruction in the artery. For example, in a typical CABG procedure a graft vessel, e.g., a section of saphenous vein, has one end attached to the aorta (proximal anastomosis) and another end attached to the coronary artery (distal anastomosis). The anastomoses are formed by suturing the graft vessel to the coronary artery and aorta, typically in an end-to-side manner. When properly formed, sutured anastomoses provide a blood-tight connection. Suturing therefore is the standard method for forming vascular anastomoses.

Although suturing produces a strong anastomosis when done correctly, the procedure is highly technical and time consuming due to the small size of the vessels being joined. The procedure is particularly difficult when carried out minimally invasively because of limited access to the heart and coronary arteries. Further, forming a hand-sewn anastomosis on a beating heart is very challenging for a majority of surgeons. Most CABG procedures are performed on a stopped heart despite recognized drawbacks associated with cardiopulmonary bypass.

Accordingly, there is a need in the art for methods and devices capable of forming vascular anastomoses quickly and easily on either a beating or stopped heart.

SUMMARY OF THE INVENTION

The invention provides methods and devices for forming anastomoses between vessels, e.g., a graft vessel and a target vessel. Pursuant to a first embodiment of the invention, a substantially suture-free anastomosis is created between the two vessels. Pursuant to a second embodiment of the invention, an anastomosis is created between a graft vessel and a target vessel so as to allow native flow through the target vessel to flow past the site of the anastomosis. The methods and devices of the invention may incorporate features of one or both of these embodiments.

According to the first embodiment of the invention, a preferred method for forming a substantially suture-free anastomosis between first and second vessels includes steps of providing a first vessel sized and configured for being joined to a second vessel having a lumen that is at least partially obstructed. At least a portion of the first vessel is placed adjacent the lumen of the second vessel so as to place the lumens of the first and second vessels in fluid communication downstream of the obstruction. The first vessel is fixed in position with respect to the lumen of the second vessel without using suture, thereby forming a substantially suture-free anastomosis between the first and second vessels.

Another preferred method carried out according to the first embodiment for forming a substantially suture-free anastomosis between a graft vessel and a coronary artery utilizes a stent-graft assembly including a stent movable between expanded and non-expanded orientations and a graft vessel attached to the stent, the graft vessel and stent being in fluid communication with each other. An opening is formed in the wall of the coronary artery and at least a portion of the stent in the non-expanded orientation is positioned in the lumen of the coronary artery. The stent is expanded into contact with the coronary artery to form a substantially suture-free anastomosis between the graft vessel and the artery.

A preferred device constructed according to the first embodiment is used to form a substantially suture-free anastomosis between first and second vessels and includes an expandable vessel coupling secured to a first vessel. The vessel coupling is in fluid communication with the first vessel and an expansion mechanism is provided for expanding the coupling. The vessel coupling is expanded to form a substantially suture-free anastomosis between the first and second vessels.

Another preferred device constructed according to the first embodiment is used to form a substantially suture-free anastomosis between a graft vessel and a target vessel and includes a stent-graft assembly comprising an expandable stent secured to a graft vessel with the lumen of the graft vessel in fluid communication with the stent. The graft vessel is adapted to be anastomosed to a coronary artery and the stent is sized and configured to fit at least partially within the lumen of the coronary artery when the stent is in the non-expanded orientation. An expansion mechanism is provided to expand the stent against the wall of the coronary artery to anastomose the stent-graft assembly to the coronary artery without suture.

According to the second embodiment of the invention, a preferred method for forming an anastomosis places a first vessel in communication with a second vessel while preserving native blood flow through the second vessel. The method includes steps of securing a first vessel to a second vessel without using suture to form a substantially suture-free anastomosis that is located distal to an obstruction in the second vessel, and allowing native blood flow in the target vessel to move past the site of the anastomosis.

A preferred device constructed according to the second embodiment is used to form an anastomosis between first and second vessels while preserving native blood flow through the second vessel. The device includes a first vessel secured to a vessel coupling in fluid communication therewith, the vessel coupling being configured to create an anastomosis between the first and second vessels while permitting native blood flow through the target vessel to move past the site of the anastomosis.

Another preferred device constructed according to the second embodiment is used to form a substantially suture-free anastomosis between a graft vessel and a target vessel while preserving native blood flow through the second vessel. The device includes a vessel coupling having first and second portions for forming an anastomosis between a graft vessel and a target vessel. The first portion of the vessel coupling is sized and configured to be coupled to a graft vessel so as to be in fluid communication with the graft vessel. The second portion of the vessel coupling is sized and configured to be coupled to a target vessel without using suture to form a substantially suture-free anastomosis that allows native blood flow through the target vessel to move past the site of the anastomosis.

BRIEF DESCRIPTION OF THE DRAWINGS

The invention will be better understood from the following detailed description of preferred embodiments thereof, taken in conjunction with the accompanying drawing figures, wherein:

FIG. 1 is a perspective view of an anastomosis device constructed according to a first embodiment of the invention, wherein the device is loaded with a graft vessel adapted to be anastomosed to a target vessel;

FIG. 2 is a transverse sectional view taken along line A—A in FIG. 1;

DESCRIPTION OF THE SPECIFIC EMBODIMENTS

Figure 3:
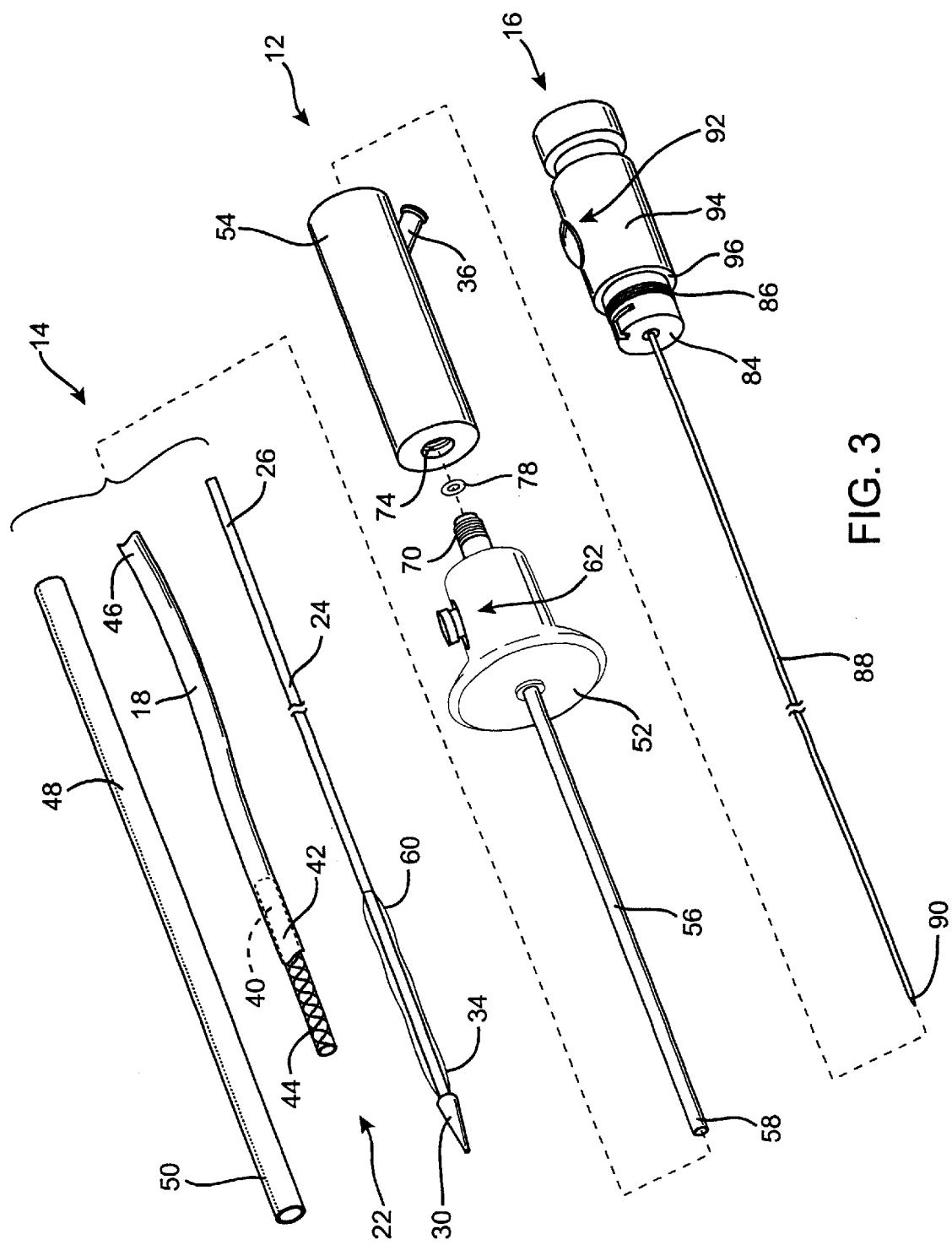
FIG. 3 is an exploded perspective view of the anastomosis device shown in FIG. 1.

Referring to FIGS. 1–6, a first preferred embodiment of a device for forming anastomoses is indicated generally by the reference numeral 10 and comprises a housing assembly 12, a shaft assembly 14 and an optional incising assembly 16. The shaft assembly 14 supports a first—or graft—vessel 18 which, according to this embodiment, is secured to a vessel coupling. The vessel coupling is in turn adapted to be secured to a second—or target—vessel to form the anastomosis (not shown in FIGS. 1–6).

According to a first embodiment of the invention, a substantially suture-free anastomosis is formed between the graft vessel and the target vessel. The term "substantially suture-free" means that the anastomosis is not a conventional hand-sewn anastomosis created by suturing the vessels together. As such, although some suture may be used, the attachment of the graft and target vessels is not created in typical hand-sewn fashion.

The vessel coupling used to form the anastomosis is preferably a conduit, and more preferably an expandable conduit, that facilitates joining the vessels to place the lumen of the first vessel in fluid communication with the lumen of the second vessel. The preferred and illustrated embodiments utilize a vessel coupling in the form of an expandable conduit because it allows the coupling to be collapsed for introduction into the target vessel and then expanded into contact with the vessel wall. ;Nonetheless, the invention may be carried out by using a coupling that comprises a non-expandable conduit, for example, a rigid tubular element securely engaged with the vessel.

Referring to FIG. 3, the expandable conduit forming the vessel coupling is a stent 20. The stent 20 is secured to the graft vessel 18 to form a stent-graft assembly 22 that is adapted to be anastomosed to a target vessel. The graft vessel 18 may comprise an autologous tissue vessel, such as a section of a saphenous vein or epigastroplegic artery, or a non-autologous tissue vessel, such as a xenograft. Further, the graft vessel 18 may comprise synthetic material, such as PTFE or ePTFE. Further still, the graft vessel could comprise a combination of tissue and synthetic material, for example, a section of saphenous vein combined with a section of ePTFE. It will be appreciated, however, that the particular type of graft vessel including the material used will vary depending on the application, including the procedure being carried out and the particular patient being treated.

Similarly, the specific construction and size of the vessel coupling will vary depending on the application. In the illustrated embodiment, the vessel coupling comprises the stent 20 which has been cut from a sheet of material (e.g., by a laser) so as to include a plurality of interwoven struts that permit the stent to move between collapsed and expanded orientations. Of course, other stent constructions may instead be used to produce a collapsible vessel coupling. For example, the stent could either be wire-formed or comprise a flat sheet of material that is unrolled to an expanded orientation. Further, the stent could be formed of various materials, e.g., nitinol, stainless steel, tantalum or titanium, and may either be self-expanding or expanded via force exerted by suitable means, e.g., a balloon or a non-inflatable expansion mechanism.

Additionally, the size, radial strength and coverage area of the stent when expanded may be selected to achieve a firm, secure attachment of the vessels. A coronary stent similar to that used in conventional CABG procedures may be used to carry out the invention, for example, a stent comprising nitinol struts with a collapsed diameter of about 1 mm, an expanded diameter of about 4 mm, and a length of about 15 mm.

As shown in FIGS. 1–3, the shaft assembly 14 supports the stent-graft assembly 22 which is used to create the anastomosis. The shaft assembly 14 includes a support member 24, preferably in the form of an elongated rod that is fixed to the housing assembly 12, which supports the stent 20 and graft vessel 18. The support member 24 has a proximal end 26 secured to the housing assembly 12 (FIG. 4) and a distal end 28 provided with a tapered surface 30 configured to dilate an opening in the wall of a vessel. A central bore 32 preferably passes through the length of the support member 24 and is sized to receive an incising element carried by the optional incising assembly 16 (FIG. 2).

The exterior of the support member 24 of the shaft assembly 14 is configured to support the stent-graft assembly 22. The illustrated and preferred embodiment uses an expandable vessel coupling (stent 20) that is moved to its expanded orientation by an expansion mechanism carried by the support member 24. The expansion mechanism may comprise a fluid-pressurized expandable element, such as a balloon, or a mechanically actuated expandable element that does not require pressurized fluid; and the expansion mechanism may be disposed inside or outside of the stent. Additionally, the vessel coupling may be a self-expanding conduit, for example, a self-expanding stent constrained by a sheath during introduction and then expanded by retracting the sheath. If the invention is to be used with a non-expandable vessel coupling, the expansion mechanism may be omitted and the support member 24 sized and configured to engage and support the vessel coupling.

The illustrated support member 24 has an expansion mechanism in the form of a balloon 34 disposed adjacent the distal end 28 of the support member (FIG. 3). The balloon 34 is expanded by a source of pressurized fluid (not shown) coupled to the housing assembly 12 via a leur fitting 36 that communicates with the interior of the housing assembly 12. The bore 32 of the support member 24 receives pressurized fluid from the interior of the housing assembly 12, and the pressurized fluid passes through one or more apertures 38 extending through the wall of the support member 24 into the interior of the balloon 34 (FIG. 4).

The graft vessel 18 is secured to the stent 20 by sutures (not shown) passing through the wall of the vessel and the wall of the stent, although any suitable means for securing the two components may be used, for example, adhesive, ultrasonic welding, clips or fasteners, etc. As shown in FIGS. 3 and 4, the proximal end 40 of the stent 20 and the distal end 42 of the graft vessel 18 preferably overlap each other a desired amount. A distal portion 44 of the stent 20 extends beyond the graft vessel 18 and is exposed for engagement with the tissue of the target vessel. The remaining length of the graft vessel 18 extends away from the stent 20 to the vessel's proximal end 46. The extent that the stent and graft vessel overlap may be different from that shown. Also, while the stent is shown disposed within the graft vessel, it could instead be disposed outside the vessel. Finally, while the illustrated stent-graft assembly includes only the stent and graft vessel, an additional layer(s) of material, such as ePTFE, may be included adjacent the stent and/or graft layer.

In use, the graft vessel 18 would be secured to the stent 20 after (or prior to) being folded or otherwise manipulated to a smaller profile more closely approximating the size of the non-expanded stent 20. In FIGS. 1–4, however, which show the stent 20 in its non-expanded orientation, for sake of clarity the graft vessel 18 is shown unfolded to a large diameter rather than collapsed to a small diameter.

Figure 4:
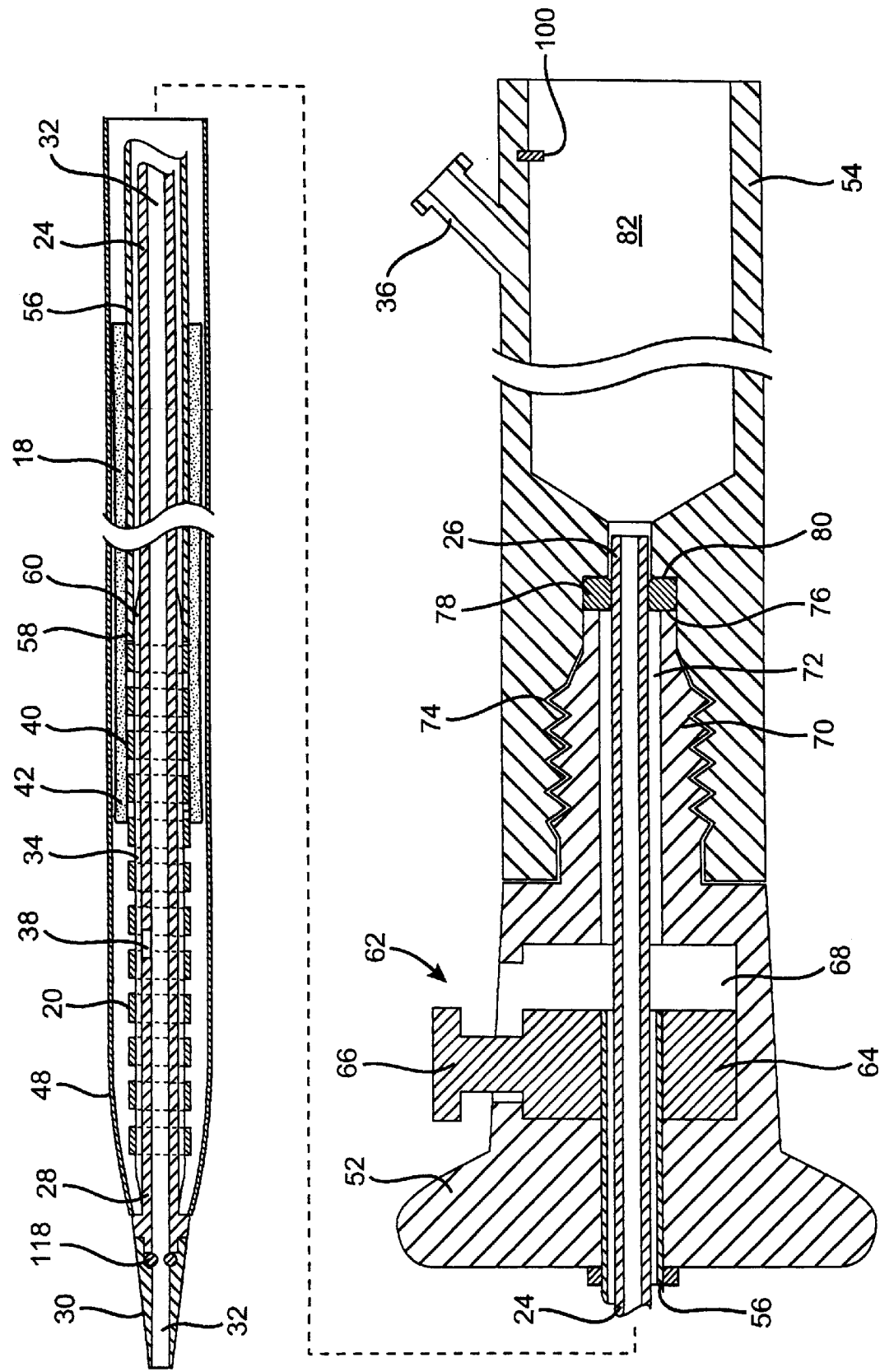
FIG. 4 is a longitudinal sectional view of the anastomosis device shown in FIG. 1.

The stent-graft assembly 22 is slid over the support member 24 and the stent 20 is positioned over the balloon 34, as shown in FIGS. 1 and 4. The stent 20 is preferably positioned so that its ends are located off the tapered ends of the balloon 34, thereby ensuring full expansion of the stent 20. The size and specific configuration of the support member 24 and the balloon 34 (or other expansion mechanism) may be selected depending on the specific application and the type of graft vessel being used. The stent may be placed over the balloon 34 and then crimped or crushed to its collapsed orientation as is known in the stent art.

The anastomosis device of the invention is preferably provided with a sheath or sleeve that overlies and protects the vessel coupling, graft vessel and target vessel during introduction of the device. In the illustrated embodiment the shaft assembly 14 includes a sheath 48 that is sized and configured to closely overlie the stent-graft assembly 22. The distal end of the sheath 48 may be tapered to fit within a step in the distal end 28 of the support member adjacent the surface 30 and is preferably tapered to provide a smooth transition between the components (as shown in FIG. 4). The sheath 48 is preferably formed of any suitable thin-walled, flexible material, e.g., polyolefin or nylon.

The sheath 48 also is preferably formed to allow it to be quickly removed from the shaft assembly 14 once the stent-graft assembly 22 has been properly located in the target vessel. In the preferred embodiment the sheath 48 comprises a peel away-type introducer having a weakened section 50 that is torn to separate the sheath 48 into two sections. The sheath 48 may have tabs (not shown) to aid in grasping and tearing the sheath along the weakened section 50. With the stent-graft assembly 22 in place, the sheath 48 is torn apart and removed in order to expose the stent 20 and the graft vessel 18.

The shaft assembly 14 extends distally away from the housing assembly 12 (FIG. 1) with the proximal end 26 of the support member 24 of the shaft assembly 14 held secure in the housing assembly 12, either permanently or removably. The housing assembly 12 comprises a first housing portion 52 detachably secured to a second housing portion 54 (FIG. 3). According to the invention, the anastomosis device preferably includes a mechanism for maintaining the vessel coupling and the graft vessel in proper position. In the illustrated embodiment the mechanism is in the form of a member that retains the stent 20 in position.

More particularly, the first housing portion 52 includes a positioning sleeve 56 that extends over a portion of the shaft assembly 14 (FIG. 4). The positioning sleeve 56 extends within the lumen of the graft vessel 18 and supports the interior of the vessel 18 when folded or collapsed for introduction into the target vessel. The sleeve 56 preferably extends distally from the housing assembly 12 a distance sufficient to position the distal end 58 of the sleeve 56 over the tapered, proximal end 60 of the balloon 28. In this position the distal end 58 of the sleeve 56 preferably abuts the proximal end of the stent 20 to hold the stent-graft assembly 22 in the desired location with respect to the shaft assembly 14 (FIG. 4).

As a result, in view of the positioning sleeve 56 overlying the proximal end of the balloon 28, the illustrated device 10 includes an actuator for selectively moving the positioning sleeve 56 in order to uncover the balloon 28 for expanding the stent 20. A suitable actuator is indicated at 62 and comprises a post having one portion 64 fixed to the positioning sleeve 56 and another portion 66 extending outside the housing for manipulation by a user's finger (FIG. 4). The post 62 is movable within a slot 68 formed in the first housing portion 52 in order to move the positioning sleeve 56 toward or away from the stent 20. The slot 68 is preferably a bayonet-type-locking slot that fixes the positioning sleeve 56 in a forward or retracted position (FIG. 3).

The first housing portion 52 is configured to be detachably secured to the second housing portion 54 and, as shown in FIGS. 1 and 4, includes a threaded extension 70 having a bore 72 which receives the proximal portion of the support shaft 24. The extension 70 is threaded into a mating recess 74 formed in the second: housing portion 54. The extension 70 also has an end surface 76 that presses an O-ring 78 against a seat 80 formed in the recess 74 in the second housing portion 54. The O-ring 78 is sized to slide over the distal end 26 of the support member 24 of the shaft assembly 14.

In use, securing the first and second housing portions 52, 54 together by threading the extension 70 into the recess 74 results in the end surface 76 forcing the O-ring 78 against the seat 80. This deforms the O-ring 78 which results in the O-ring frictionally engaging the proximal end 26 of the support member 24, as shown in FIG. 4. Separating the first and second housing portions 52, 54 removes the force on the O-ring 78 to release the support member 24 and allow the shaft assembly 14 to be removed from the device 10.

It should be appreciated that an anastomosis device constructed according to the invention, in contrast to the illustrated embodiment, could be formed with no removable or detachable components. For example, the housing assembly 12 of the preferred embodiment shown in FIGS. 1–6 could comprise one section that removably (or irremovably) supports the shaft assembly 14, although a multi-piece housing assembly may be preferred for cost or manufacturing reasons. Further, the device could be constructed as a one-piece instrument with no separable components, wherein the device is simply loaded with a graft vessel and vessel coupling. The device may be formed as a disposable instrument, a reusable instrument capable of being sterilized, or a combination and disposable and reusable components.

Referring to FIG. 4, the second housing portion 54 includes an internal chamber 82 that communicates with the pressurized fluid port 36. Thus, in use pressurized fluid passes through the port 36 into the chamber 82 and then flows into the bore 32 of the housing assembly support member 24. As explained above with respect to FIG. 2, the pressurized fluid passes through the aperture(s) 38 in the support member 24 and expands the balloon 34. The O-ring 78, in addition to retaining the support member 24 in housing assembly 12, seals against the exterior of the support member 24 to prevent pressurized fluid escaping the chamber 82 other than through the bore 32 in the support member 24.

Figure 5A:
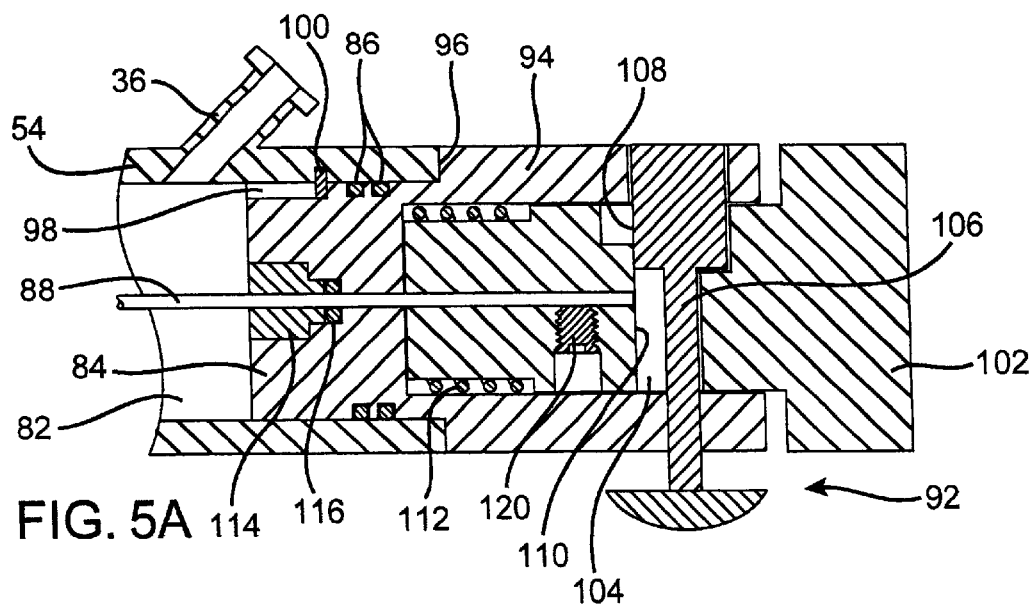
FIG. 5A is a longitudinal sectional view illustrating a portion of the anastomosis device shown in FIG. 4 along with an incising assembly, wherein the incising assembly is shown in a first position.

The device 10 is preferably provided with means for preventing the escape of pressurized fluid from the chamber 82 via the end opposite the first housing portion 52. As shown in FIG. 5A, in which the incising assembly 16 is shown coupled to the device 10, the fluid is blocked from escape by a boss 84 carried by the incising assembly 16: The boss 84 is sized to be received within the chamber 82 in a press fit. The boss 84 is preferably provided with one or more seals, such as O-rings 86, which press against the interior of the second housing portion 54 to further seal the fluid in the chamber 82. It should be appreciated that alternative mechanisms may be used to deliver pressurized fluid to the shaft assembly and to seal the respective components together.

Figure 5B:
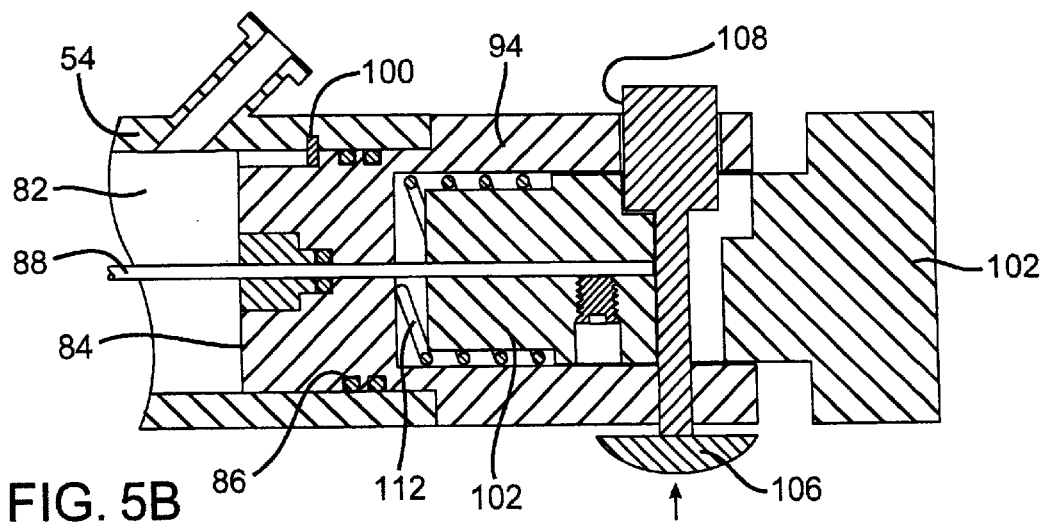
FIG. 5B is a longitudinal sectional view of the portion of the anastomosis device and the incising assembly shown in FIG. 5A, wherein the incising assembly is shown in a second position.
Figure 6:
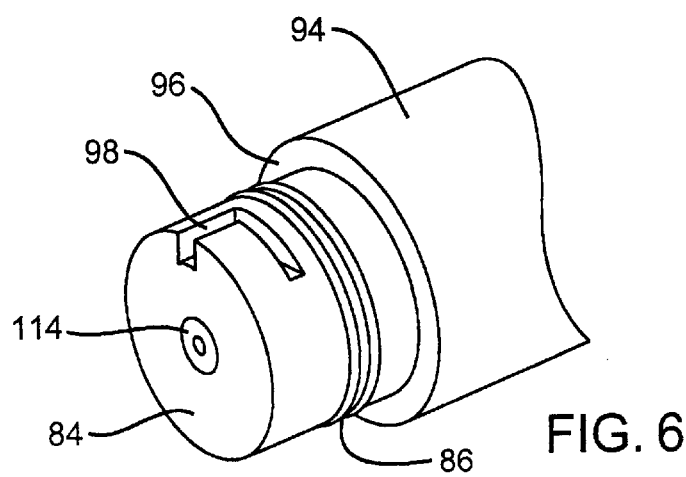
FIG. 6 is a schematic perspective view of a portion of the incising assembly shown in FIGS. 5A–5B.

The optional incising assembly 16 may be provided for initially penetrating the wall of the target vessel and comprises an incising element 88 having a sharpened tip 90 which extends beyond the distal end 28 of the support member (FIG. 1). The incising assembly 16 is provided with an actuator 92 for selectively extending or retracting the sharpened tip 90 with respect to the housing assembly support member 24 (FIGS. 5A–5B). The sharpened tip 90 of the incising element 88 and the tapered surface 30 of the distal end 28 of the support member 24 are preferably formed with mating profiles to provide a smooth transition between the components that aids in dilating an incision formed in the vessel wall.

The incising assembly 16 includes a hub 94 adapted to be secured to the proximal end of the second housing portion 54. The boss 84 extends from the hub 94 and defines a rim 96 that abuts the proximal end of the second housing portion 54. The incising assembly 16 and the housing assembly 12 may be secured by, any desired coupling mechanism. In the illustrated embodiment, in which the incising assembly 16 is detachable from the housing assembly 12, the mechanism comprises a bayonet coupling including a slot 98 in the boss 84 of the incising hub 94 and a pin 100 carried by the second housing portion 54 (FIG. 5A). This or another type of quick-connect coupling is preferred as it allows the incising assembly 16 to be easily attached to or detached from the housing assembly 12.

The incising assembly actuator 92 is used to selectively extend or retract the incising element 88 with respect to the shaft assembly 14. The preferred actuator 92 comprises a block 102 movably disposed in a recess formed in the proximal end of the hub 94. The block 102 has a passage 104 in which a locking pin 106 is disposed, the pin 106 having a stop surface 108 that contacts a surface 110 of the block 102. A spring 112 is disposed in the recess along with the block 102 and is located between the exterior of the block 102 and the interior of the hub 94. In the position shown in FIG. 5A, wherein the incising element 88 is extended, the stop surface 108 of the locking pin 106 contacts the surface 110 to hold the block 102 and the incising element 88 in position against the biasing force exerted by the spring 112.

The actuator 92 is used to retract the incising element 88 by moving the locking pin 106 relative to the incising hub 94 from the position shown in FIG. 5A to the position shown in FIG. 5B. Pressing the locking pin 106 moves the stop surface 108 of the pin off of the stop surface 110 of the block 102. This results in the spring 112 forcing the incising block 102 in a proximal direction because the locking pin 106 is now free to ride in the passage 104 in the block 102. The actuator 92 is constructed so that the block 102 is moved proximally a distance sufficient to ensure that the sharpened tip 90 of the incising element 88 moves within the bore 32 of the shaft assembly support member 24.

The incising element 88 preferably passes through a fitting 114 positioned in the boss 84 of the incising hub 94, which fitting 114 may be provided with a seal to minimize or prevent the escape of pressurized fluid from the chamber 82, such as an O-ring 116 which seals against the exterior of the incising element 88. The incising element 88 also preferably passes through an O-ring 118 carried by the distal end 28 of the shaft assembly support member 24 (FIG. 4). The O-ring 118 is disposed in the bore 32 of the support member and seals against the exterior of the incising element 88 to aid in sealing pressurized fluid in the chamber 82. The incising element 88 may be: fixed to the incising assembly by any suitable means, such as a set screw 120 disposed in a bore formed in the incising block 102 (FIGS. 5A–5B). It will be recognized that an alternative actuator may be used in lieu of the actuator 92 illustrated and described herein.

In the illustrated and preferred embodiment, the incising assembly 16 is a separate component that is detachably secured to the housing assembly 12. It will be recognized, though, that the incising assembly 16 could instead be permanently secured to the device 10 or formed as an integral part of the device. Further, it should be understood that the device 10 may be used without an incising assembly for piercing tissue, for example, by placing the shaft assembly 14 of the device through a cut-down or other surgically-formed opening in a vessel wall. As another alternative, the support member 24 may have a bore 32 which, instead of or in addition to receiving an incising element, may be used to pass the device over a guide wire or catheter that has been introduced into the lumen of a vessel.

One benefit of providing a bore 32 through the support member 24 of the anastomosis device 10 is that the stent-graft assembly 22 is protected from contact with any element located in the bore. Thus, an incising element, guide wire, guide catheter, etc., may be used without risk of damage to the stent-graft assembly 22. The bore 32 thus facilitates the use of removable or exchangeable guide and incising elements to be used with the device. Moreover, the bore 32 may be configured to act as a flashback lumen to indicated to the user that the device has entered a lumen containing blood, for example, a coronary artery or heart chamber.

An exemplary method for forming an anastomosis according to the first embodiment of the invention will be described with respect to FIGS. 7–12. These Figures show one preferred use of the device described above, namely, creating an anastomosis between two vascular structures. It will be appreciated, however, that application of the invention is not so limited. The term anastomosis as used herein refers to the joining of any two or more hollow body structures so as to place their interiors in fluid communication. As such, it will be understood that the anastomosis of vascular structures shown in the drawing Figures is an exemplary application only.

Figure 7:
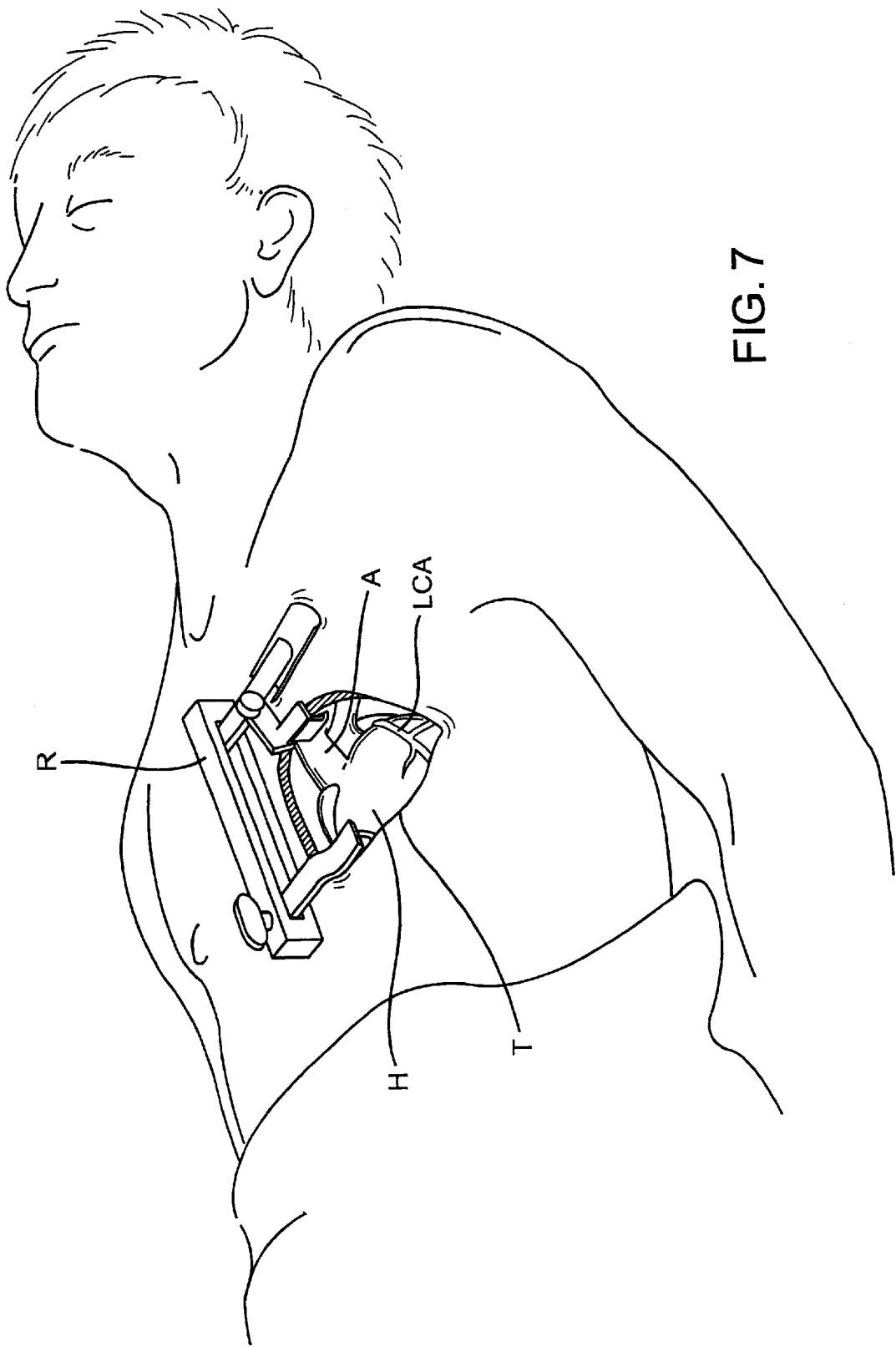
FIG. 7 is a schematic view of a patient prepared to undergo a cardiovascular surgical procedure, the patient's heart being exposed via a retractor positioned in a thoracotomy formed in the patient's chest.

FIG. 7 schematically depicts a patient who has been prepared to undergo a cardiovascular surgical procedure. A thoracotomy T is formed in the patient's chest by making an incision between two ribs (not shown) to provide access to the thoracic cavity. A retractor R may be used to spread the ribs and increase access to the heart H and great vessels. The retractor is preferably of a type that raises one side of the incision with respect to the other side to increase the working space around the heart. Any suitable retractor may be used, for example, one of the commercially available rib retractors currently used in minimally invasive cardiac surgery. As shown, the retractor R provides considerable access to the surfaces of the heart H and great vessels including the aorta A. The left side of the heart as well as the left coronary artery LCA is easily accessible via the thoracotomy T.

Figure 8:
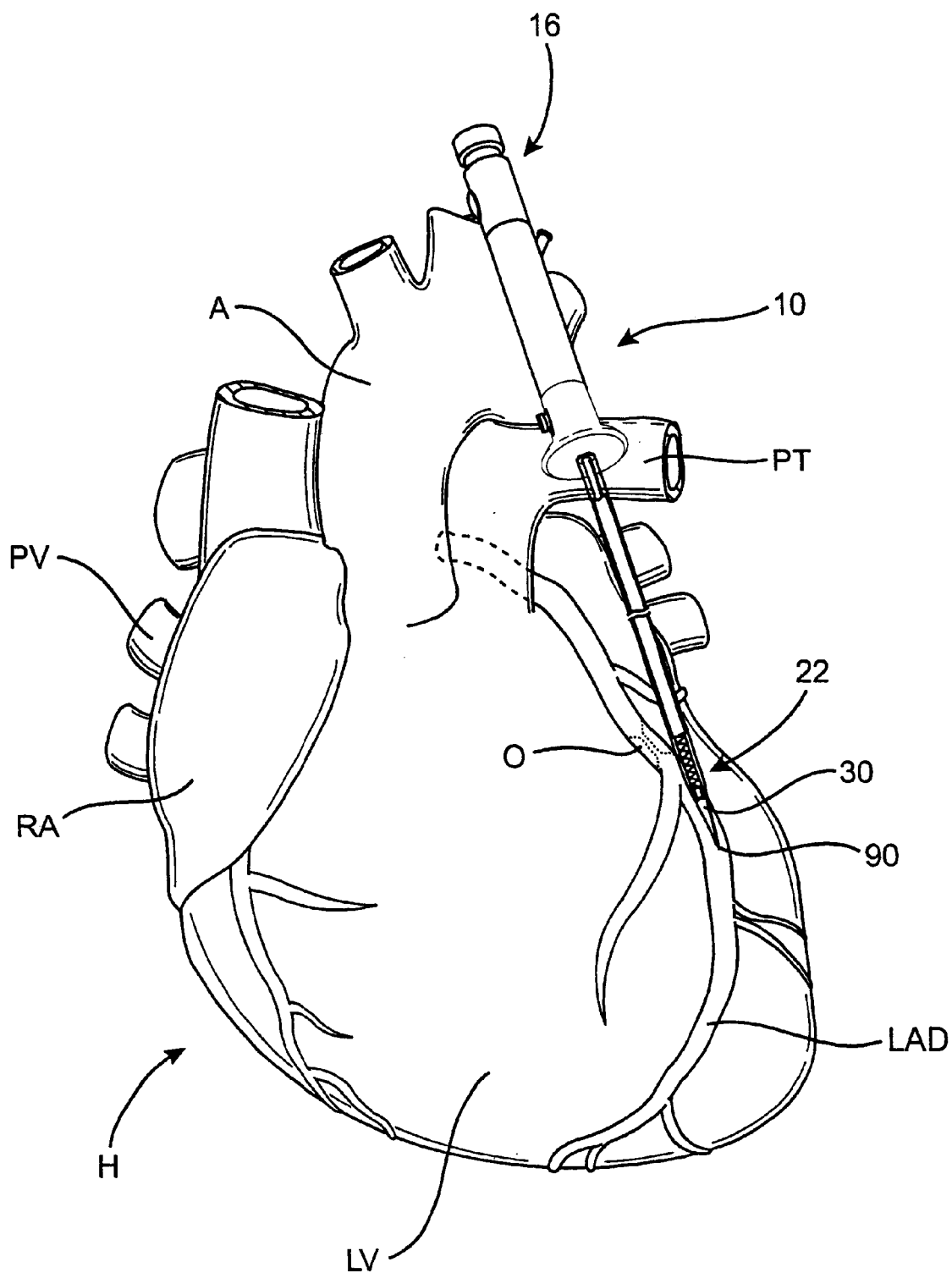
FIG. 8 is a perspective view of the heart shown in FIG. 7 with an obstructed coronary artery, wherein the anastomosis device shown in FIG. 1 is located adjacent the coronary artery.

FIG. 8 shows the heart H in isolation along with an anastomosis device 10 constructed as described above. FIG. 8 is an anterior view of the heart H showing the left ventricle LV, right atrium RA, aorta A, pulmonary trunk PT and pulmonary veins PV. The left coronary artery, including the circumflex branch and the left anterior descending branch LAD, is visible in this view, as is the right coronary artery RCA. The coronary arteries run along the heart wall and deliver oxygenated blood to the myocardial tissue. An occlusion or blockage 0 partially (or completely) obstructs the lumen of the LAD, which results in inadequate or no blood flow to the heart wall tissue fed by the portion of the LAD that is downstream of the occlusion 0.

As shown in FIG. 8, the tip 90 of the incising element 88 extends beyond the distal end of the device 10 and is used to pierce the wall of the LAD. The device 10 may be manipulated with respect to the heart H in order to obtain the most advantageous angle of entry into the coronary artery. The particular manner in which the device 10 is oriented will of course depend on the specific application, including the particular vessel being treated and whether the procedure is being carried out, for example, in an open-chest manner via a median sternotomy or a minimally invasive manner via one or more smaller surgical openings (such as the thoracotomy T in FIG. 7). In any event, the device 10 is held at an optimal position for passing the tip 90 of incising element 88 through the wall of the LAD.

Figure 9:
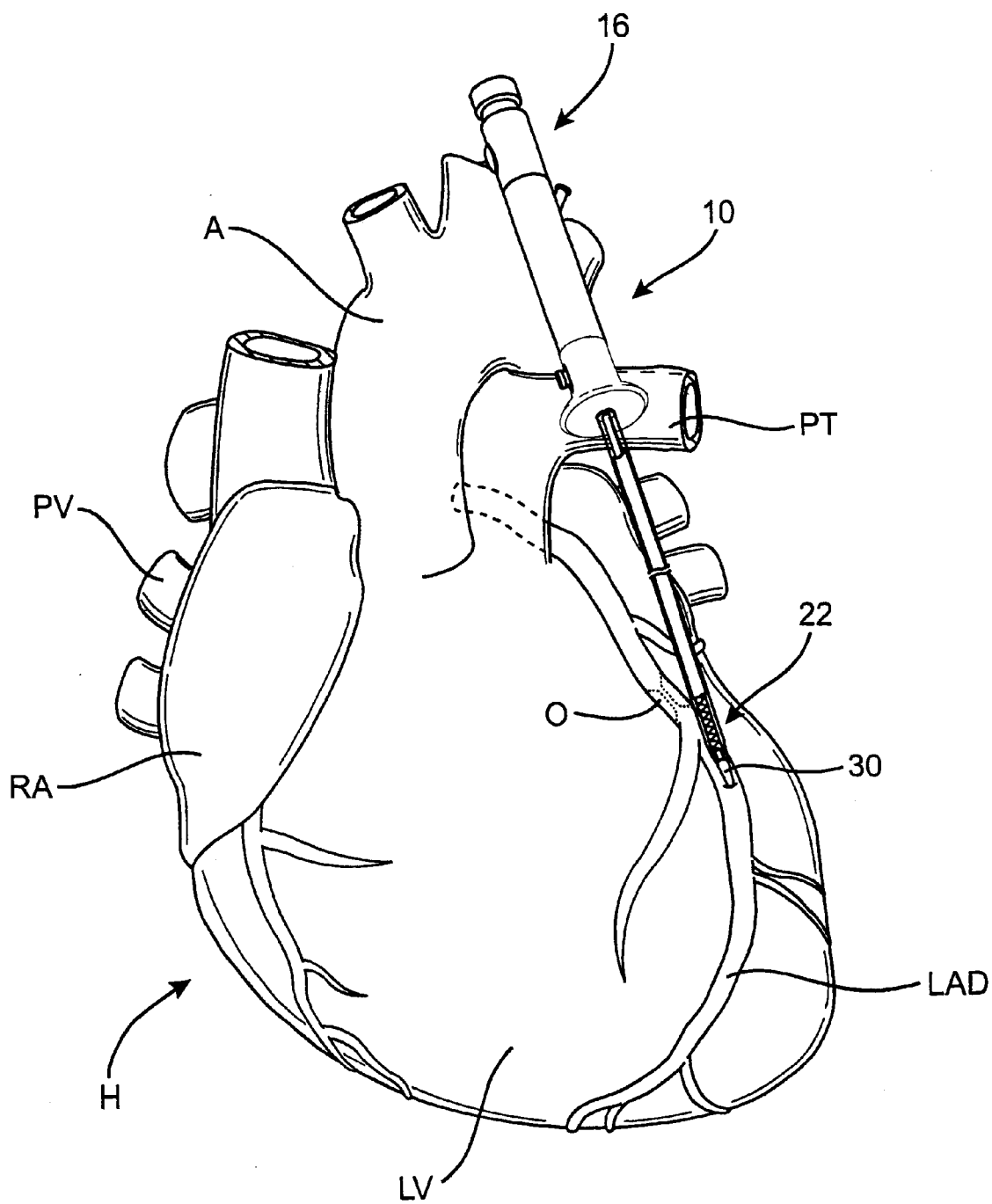
FIG. 9 is a perspective view of the heart shown in FIG. 8, wherein the anastomosis device is shown being introduced through the wall of the coronary artery.
Figure 10A:
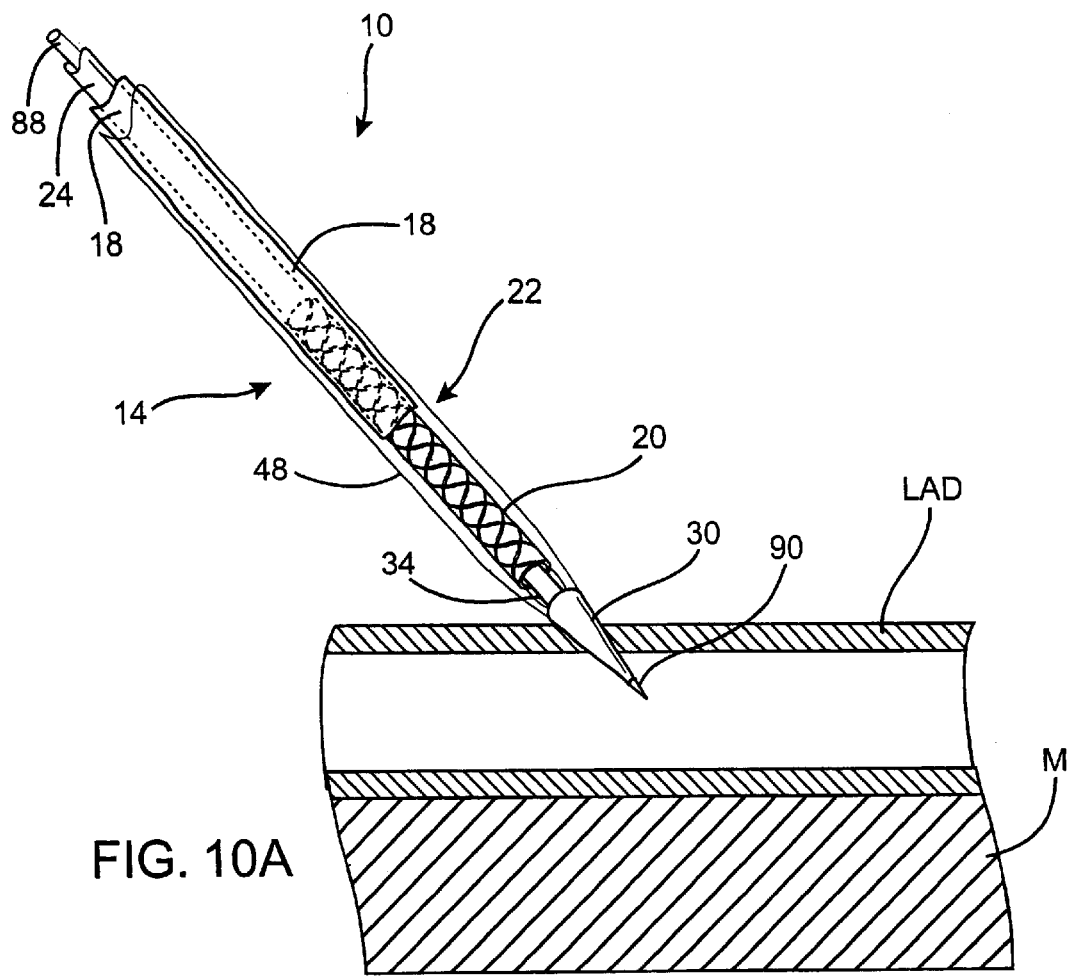
FIG. 10A is an enlarged sectional view of a portion of the heart shown in FIG. 9 illustrating the distal end of the anastomosis device positioned in the lumen of the coronary artery.
Figure 10B:
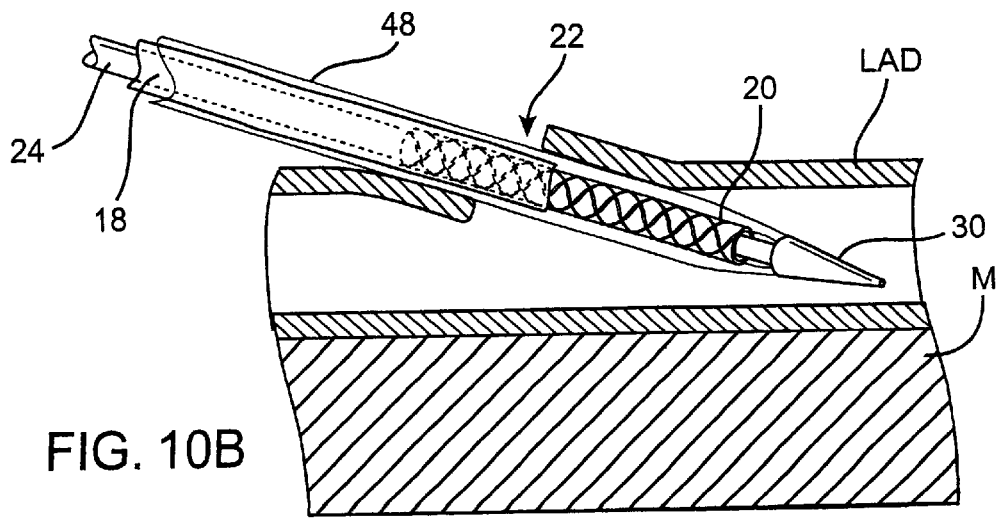
FIG. 10B is an enlarged sectional view of the portion of the heart shown in FIG. 10A illustrating the anastomosis device after an incising element has been retracted.

FIG. 9 shows the heart H and the device 10 after the sharpened tip 90 has pierced the wall of the LAD. FIG. 10A is a sectional view corresponding to FIG. 9 but showing only the portion of the LAD and the heart wall M adjacent the point of entry of the device 10. As can be seen in FIG. 10A, the tip 90 of the incising element 88 is exposed inside the lumen of the LAD. The incising element 88 is thus retracted once the distal end of the device 10 has been passed through the wall of the LAD. Once this has been done, the device 10 is introduced further into the LAD, preferably by angling the device as shown in FIG. 10B. The device 10 is moved into the lumen of the LAD a sufficient amount to place the stent-graft assembly at a predetermined location in the lumen of the LAD.

The invention may be provided with means for indexing the position of the device 10 in order to control the position of the stent-graft assembly 22 with respect to the target vessel such as the LAD. Suitable means for indexing the position of the stent-graft assembly 22 include markings placed along the shaft assembly 14, for example, the sheath 48, that may be read with respect to the wall of the target vessel to determine the position of the stent-graft assembly 22 with respect to the target vessel. Other means include one or more stops carried by the shaft assembly 14 for engaging or contacting tissue to control the position of the stent-graft assembly 22 in the target vessel. Additionally, using a sheath 48 through which the stent-graft assembly 22 can be seen allows the user to visually confirm proper positioning of the stent-graft assembly 22 in the target vessel.

Figure 10C:
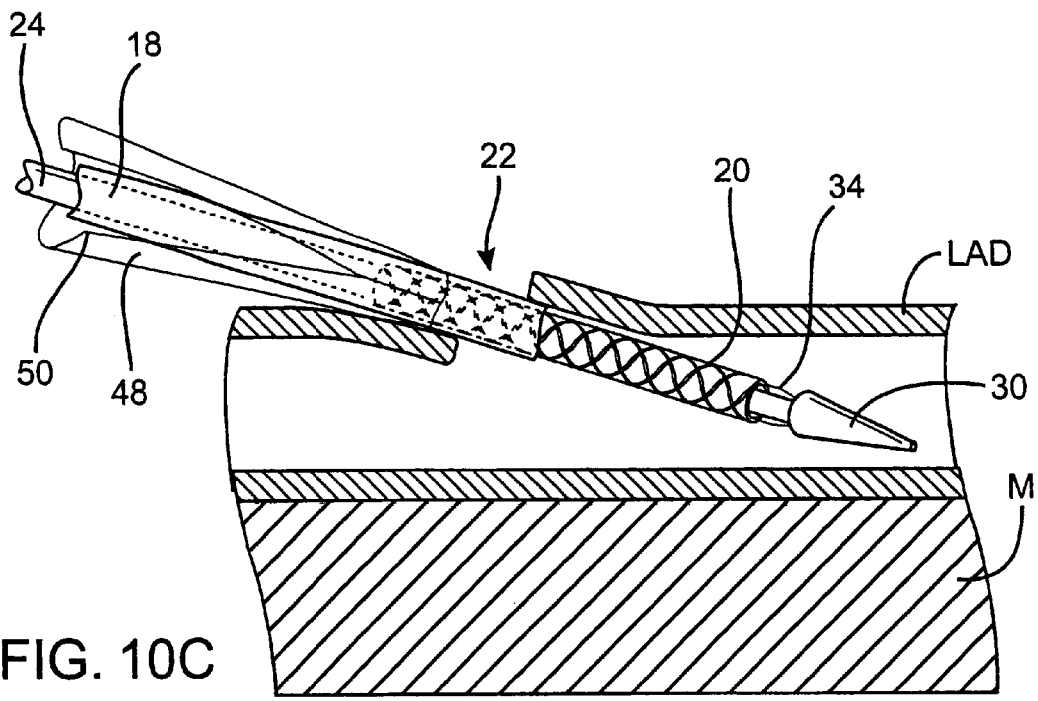
FIG. 10C is an enlarged sectional view of the portion of the heart shown in FIG. 10B illustrating the anastomosis device during the removal of a protective sheath overlying a vessel coupling and a graft vessel.

Once inside the LAD, the shaft assembly 14 of the device 10 can be moved without risk of tissue damage because the incising tip 90 has been retracted (FIG. 10B) and the tapered dilating portion 30 of the support member 24 has a generally a traumatic configuration. Referring to FIG. 10C, the device is shown after the sheath 48 has been partially torn apart along the weakened section 50. The remaining length of the sheath 48 is split apart to expose the formerly covered portion of the stent-graft assembly 22. The positioning sleeve 56 is then retracted to uncover the proximal end of the balloon 34. At this point the stent-graft assembly 22 is ready to be expanded, and secured to the LAD.

Figure 10D:
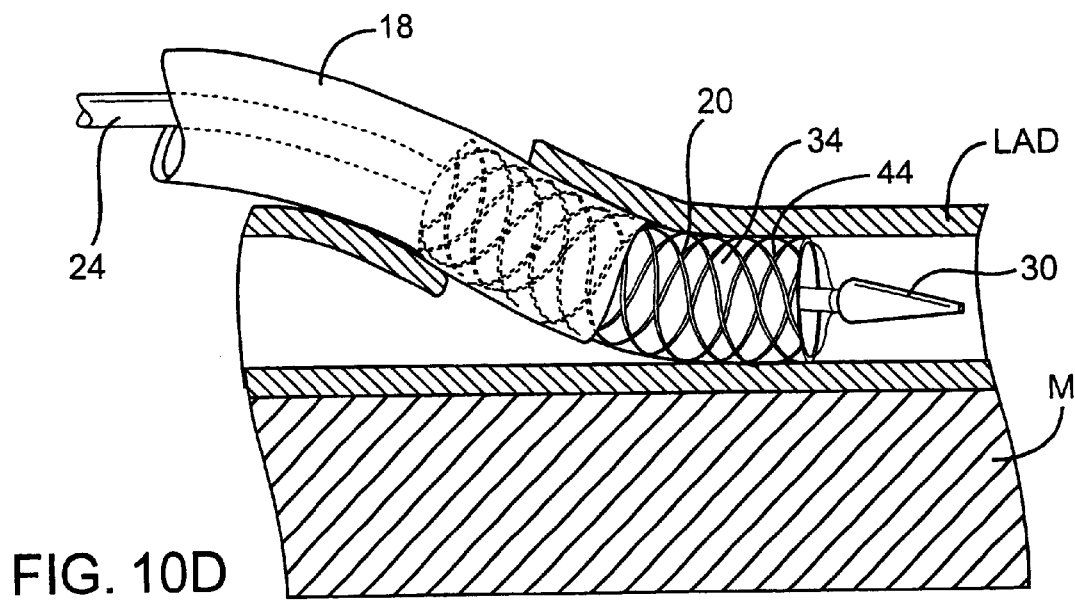
FIG. 10D is an enlarged sectional view of the portion of the heart shown in FIG. 10C after the vessel coupling has been used to secure the graft vessel to the coronary artery.

Next, the device 10 is coupled to a source of pressurized fluid (not shown) via the port 36 and the fluid enters the chamber 82 in the second housing portion 54 and passes into the bore 32 of the support member 24. The fluid enters the interior of the balloon 34 via aperture(s) 38 and expands the balloon 34 and the stent-graft assembly 22, as shown in FIG. 10D. The stent 20 preferably expands to a maximum radial strength position in which the stent struts press firmly into the tissue of the wall of the target vessel. The exposed portion 44 of the stent 20 moves against the wall of the LAD to securely anchor the stent 20 (and the graft vessel 18 attached thereto)i to the LAD. The remaining portion of the stent 20 is also expanded which presses the distal end 42 of the graft vessel 18 against the tissue of the LAD to form a blood-tight seal, the distal end 42 preferably being within the LAD lumen.

As can be seen in FIG. 10D, the shaft assembly 14, and in particular the stent-graft assembly 22, support member 24 and balloon 34 are preferably relatively flexible to permit the shaft assembly 14 to bend during the procedure. The degree of flexibility imparted to the shaft assembly 14 of the device 10, as well as the dimensions of the device 10, may vary depending on the application and user preference. The device 10 could be formed with a shaft assembly 14 that is curved, malleable so as to be bendable to a selected configuration, or articulated with a movable portion that may be controlled or steered, for example, by known mechanisms.

As an example of a range of possible constructions, the device 10 may be relatively short with the shaft assembly 14 substantially rigid for use in an open-chest procedure. Alternatively, the device 10 may be relatively long with the shaft assembly 14 rigid or flexible for use in a minimally invasive procedure. As yet another alternative, the device may be longer (with the shaft assembly 14 flexible or rigid) for use in an endoscopic procedure, wherein the actuators for controlling the device components are located at the proximal portion or end of the device to allow remote deployment of the vessel coupling.

Figure 10E:
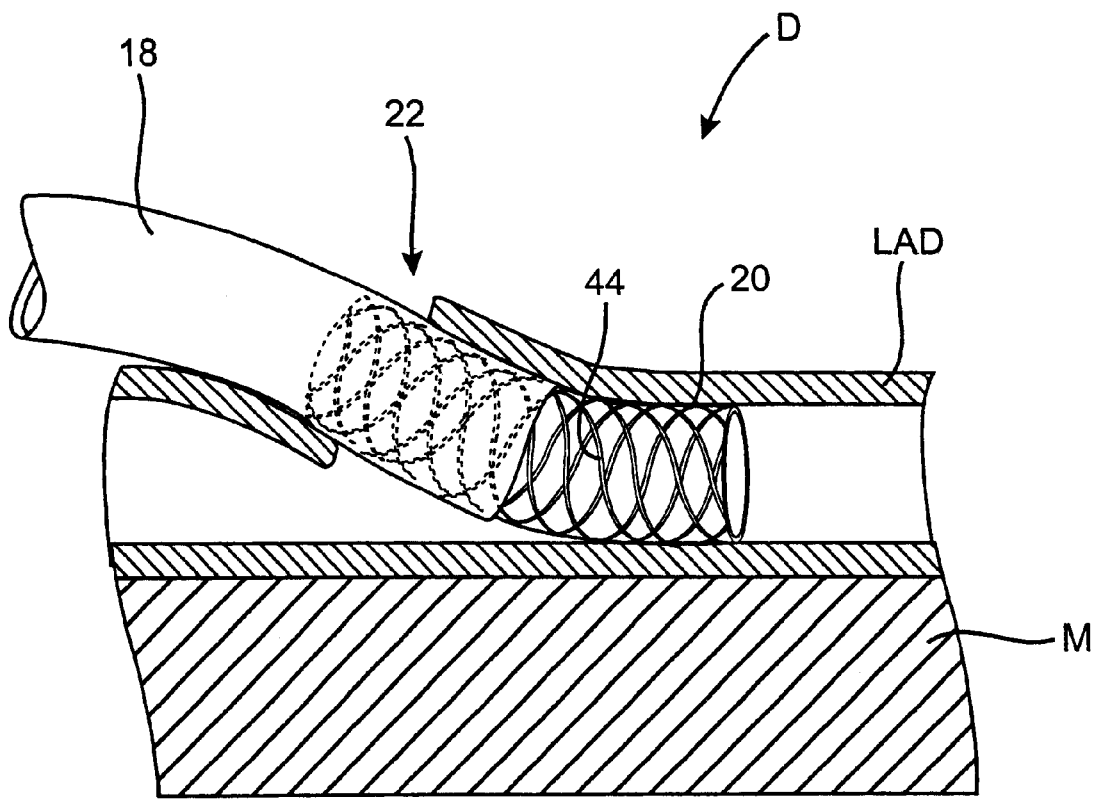
FIG. 10E is an enlarged sectional view of the portion of the heart shown in FIG. 10D illustrating the completed distal anastomosis.

From the position shown in FIG. 10D, the balloon 34 is taken down by drawing a vacuum through the bore 32 of the support member 24, and is then removed to leave the stent-graft assembly 22 expanded against the LAD. The resulting configuration is shown in FIG. 10E. In the illustrated embodiment, the exposed distal portion 44 of the stent 20 is disposed entirely within the lumen of the LAD. The proximal portion 40 of the stent 20 (along with the overlapping distal end 42 of the graft vessel 18) is disposed partly within the lumen of the LAD and partly outside the lumen of the LAD. It may be desirable to place the stent-graft assembly 22 (or other vessel coupling) so that a portion extends through the opening formed in the wall of the target vessel to aid in maintaining the anastomosis patent at the junction of the vessels. Additionally, having an expanded portion of the stent 20 extend through the opening in the target vessel enhances the seal formed at the vessel junction. It will nevertheless be recognized that:the relative position of the vessels and vessel coupling may be varied from the exemplary: configuration illustrated in FIG. 10E.

Figure 11:
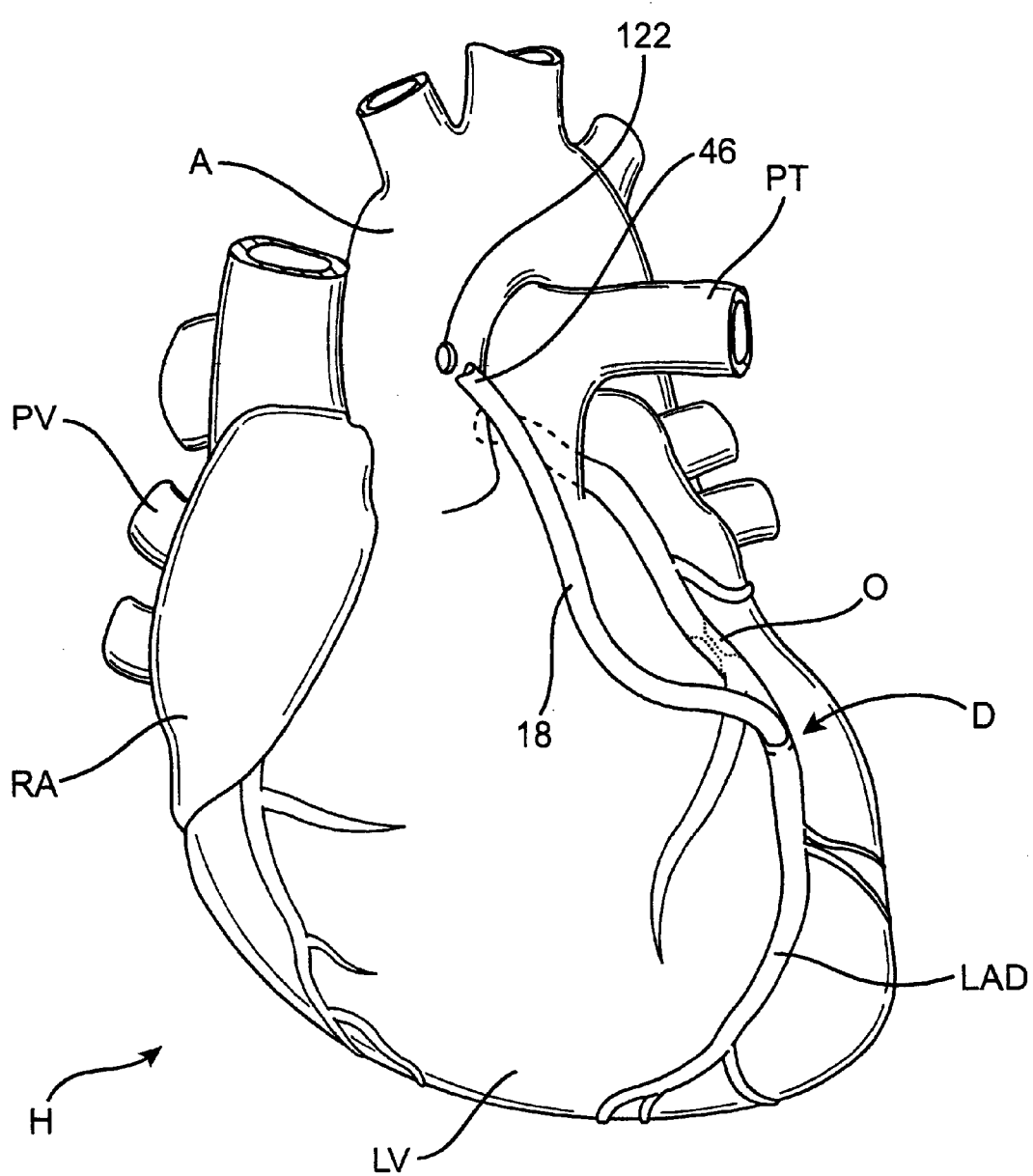
FIG. 11 is a schematic perspective view of the exterior of the heart shown in FIG. 10E illustrating the completed distal anastomosis, as well as an aortotomy formed in the aorta in order to perform a proximal anastomosis between the free end of the graft vessel and the aorta.
Figure 12:
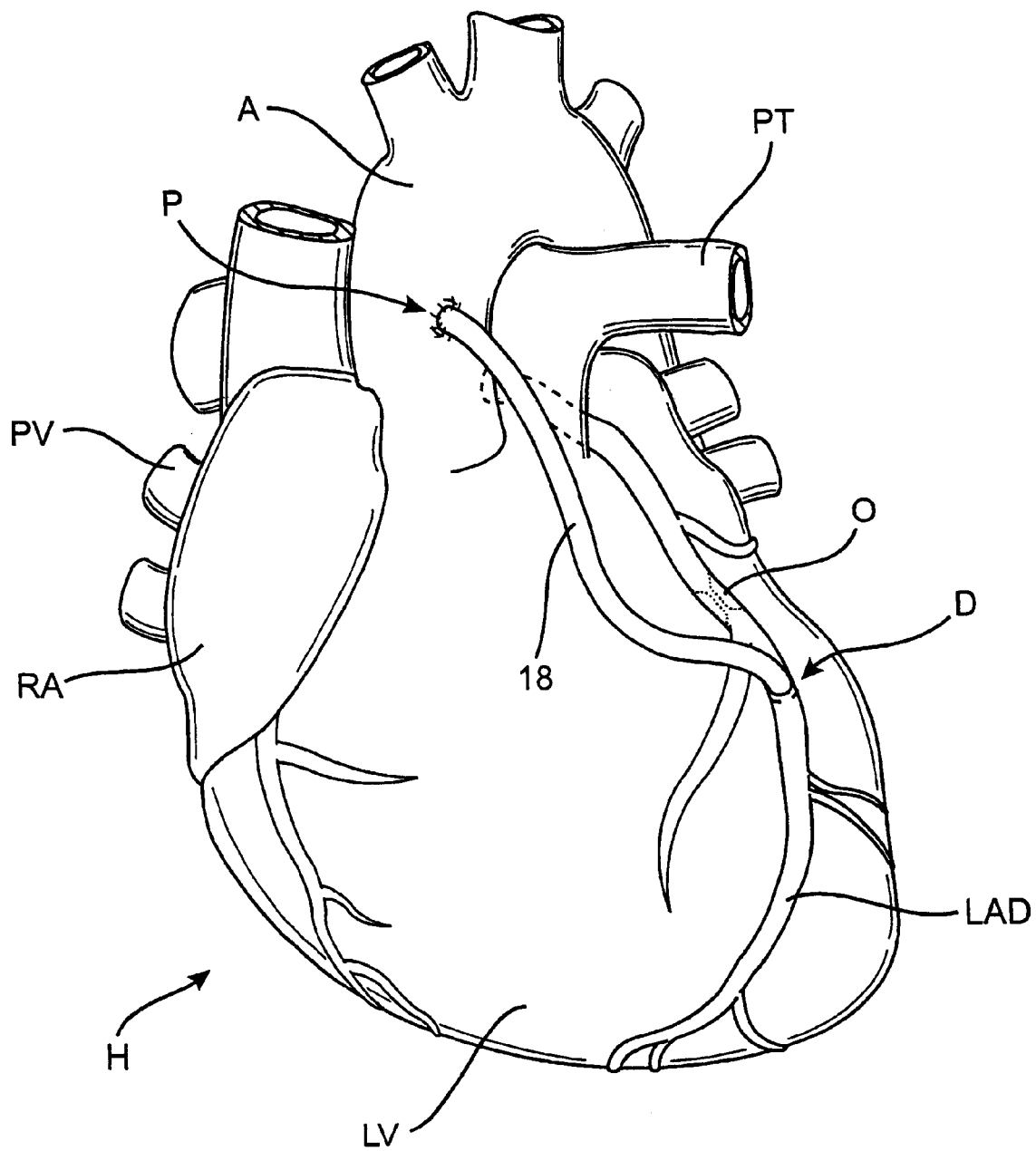
FIG. 12 is a schematic perspective view of the heart shown in FIG. 11 illustrating the completed proximal anastomosis formed by suturing the free end of the graft vessel to the aorta.

FIG. 11 illustrates the anastomosis depicted in FIG. 10E from the exterior of the heart H. The graft vessel 18 has been attached to the LAD downstream of the obstruction O as part of a CABG procedure to form a distal anastomosis D. Next, the proximal end 46 of the graft vessel 18 is prepared as known in the art for anastomosis to a source of oxygenated blood, such as the aorta A. An aortotomy 122 is formed in the wall of the aorta, for example, by making an incision and using an aortic punch (not shown). As shown in FIG. 12, the proximal end 46 of the graft vessel 18 is then sutured to the aorta in conventional fashion to form the proximal anastomosis P and complete the CABG procedure.

An anastomosis device constructed according to the first embodiment of the invention thus may be used to create a substantially suture-free anastomosis as compared with conventional, hand-sewn sutured anastomoses. The anastomosis may be characterized as suture-free even if the graft vessel is sutured to the vessel coupling (as shown) in view of the fact the vessels are not attached by being stitched together. The invention forms a distal anastomosis during a CABG procedure much more quickly and easily than suturing the end of the graft vessel to the side of the coronary artery. As cardiovascular treatments have continued to become more and more minimally invasive with reduced access to the heart, suturing these extremely small blood vessels together has become more difficult and time consuming. The invention creates a distal anastomosis by simply cannulating the coronary artery to position and secure the vessel coupling and graft vessel to the artery. This is a significant advantage in that forming the distal anastomosis according to the invention can be done relatively quickly and easily during a minimally invasive, beating heart procedure.

The embodiment described above forms the anastomosis by placing a portion of the vessel coupling and/or graft vessel in the lumen of the target vessel, which may obstruct the lumen of the target vessel. For example, as shown in FIG. 10E, the lumen of the LAD may be substantially (or even completely) occluded by the stent-graft assembly 22 once the assembly has been expanded to its final position. As a result, blood flowing from upstream of the anastomosis site is hindered or prevented from flowing distally by the stent-graft assembly 22. In the case of a coronary artery, the stent-graft assembly 22 could limit or block-native blood flow through the artery, i.e., blood flowing through the artery from a proximal source, e.g., the aorta. Many patients undergoing a CABG procedure will have some native proximal blood flow in one or more obstructed arteries. It therefore would be desirable to form an anastomosis that preserves such native blood flow in the target vessel.

According to the second embodiment of the invention, methods and devices are provided for forming an anastomosis between a graft vessel and a target vessel while preserving native blood flow through the target vessel. That is, blood flowing through the target vessel prior to forming the anastomosis is free to flow past the site of the anastomosis. The anastomosis may be created using a vessel coupling including a first portion secured to the graft vessel and a second portion secured to the target vessel without blocking blood flow through the target vessel. The anastomosis is preferably, but not necessarily, substantially suture-free as in the first embodiment of the invention.

Figure 13:
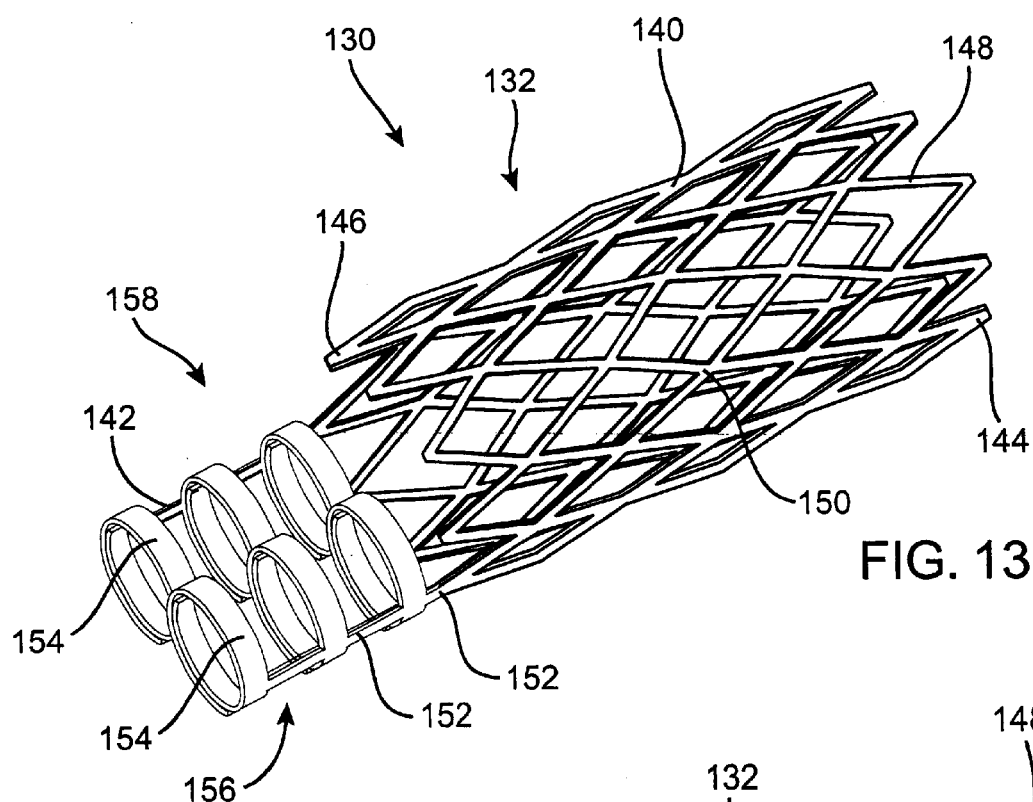
FIG. 13 is a perspective view of a vessel coupling constructed according to another embodiment of the invention for forming an anastomosis between a graft vessel and a target vessel that preserves native blood flow through the target vessel, wherein the vessel coupling is shown in a collapsed orientation.
Figure 14:
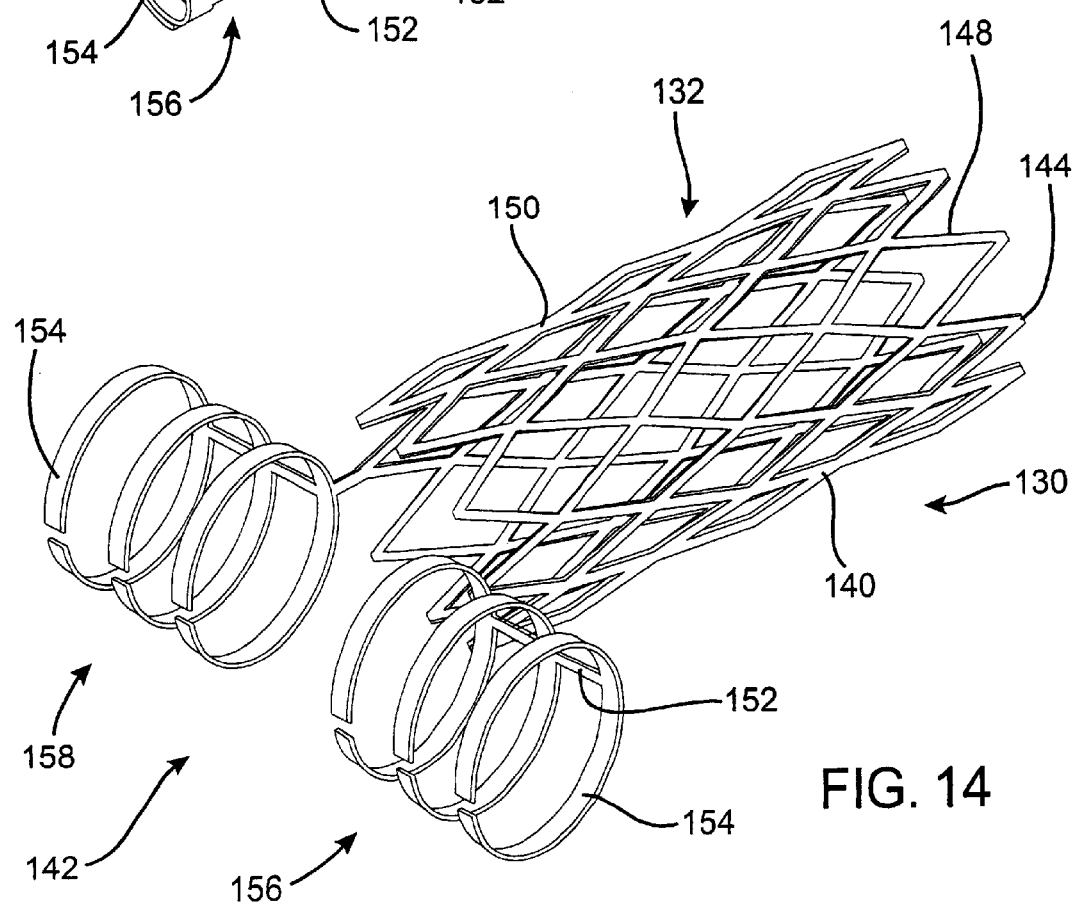
FIG. 14 is a perspective view of the vessel coupling shown in FIG. 13 in an expanded orientation.

One preferred device constructed according to the second embodiment comprises a vessel coupling indicated by reference numeral 130 in FIGS. 13–18. The vessel coupling 130 is in the form of a stent 132 that is secured to a graft vessel 134 to form a stent-graft assembly 136. The stent-graft assembly 136 is adapted to be secured to a target vessel so as to place the lumens of the graft and target vessels in fluid communication. FIG. 13 shows the stent 132 in its collapsed orientation while FIG. 14 shows the stent 132 in its expanded orientation. The stent 132 comprises a body 140 joined to a frame 142, each of which is preferably movable between collapsed and expanded orientations. For sake of clarity, the stent body 140 is not shown fully collapsed to its low profile orientation. The stent body 140 has a proximal end 144 and a distal end 146, and comprises a plurality of struts 148 interconnected at nodes 150. The distal end 146 of the stent body 140 is attached to the frame 142 by bands 152.

The frame 142 includes at least one, and preferably a plurality of frame elements 154 each of which collapses when the stent 132 is collapsed. The frame elements 154 are connected to each other and to the stent body 140 by bands 152 which serve to maintain the frame elements 154 properly oriented. The illustrated embodiment includes two separate sets 156, 158 of frame elements 154, each set being independently movable with respect to the stent body 140. It will be understood that the number, size and shape of the frame elements may vary from that shown in the Figures—as long as the frame 154 is constructed to not block blood flow once the frame has been positioned in the lumen of a target vessel.

The frame elements 154 may take any form and in the illustrated embodiment comprise loops or coils that collapse with the stent 132. It will be appreciated that the frame elements could be shaped differently and could also collapse in a different manner than illustrated in FIG. 13, for example, by simply being crushed or smashed to a low profile orientation. FIG. 14 shows the stent 132 after it has been expanded from the collapsed orientation shown in FIG. 13. The stent body 140 expands radially in a manner known, per se, with the struts 148 moving relative to one another.

The illustrated frame 154 undergoes two movements in order to expand (or collapse) with the stent body 140. As the vessel coupling 130 expands, the sets 156,-158 of frame elements 154 move apart from each other while the individual frame elements 154 uncoil and expand to the position shown in FIG. 14. The orientation of the vessel coupling 130 shown in FIG. 14 corresponds to the deployed position of the coupling in a completed anastomosis.

The stent 132 forming part of the vessel coupling 130 may have any suitable construction that permits the stent to be easily collapsed and expanded. In the preferred embodiment the stent 132 is formed of a shape memory alloy (such as nitinol) that has been shape set to the expanded orientation shown in FIG. 14. Other materials, e.g., stainless steel or titanium, may be used as well. The stent 132 is preferably self-expanding and may be collapsed and placed in a sheath (not shown in FIGS. 13–18) that maintains the stent 132 in this orientation. Alternatively, the stent 132 could be expanded by a suitable expansion mechanism, such as a balloon(s). The size of the stent 132 (or other vessel coupling that permits flow through the target vessel after forming the anastomosis ) may be selected depending on various factors including the procedure being carried out and the patient being treated. The illustrated stent 132 is sized and configured for use in forming a distal anastomosis between a graft vessel, such as a section of saphenous vein, and a coronary artery containing an obstruction.

Figure 15:
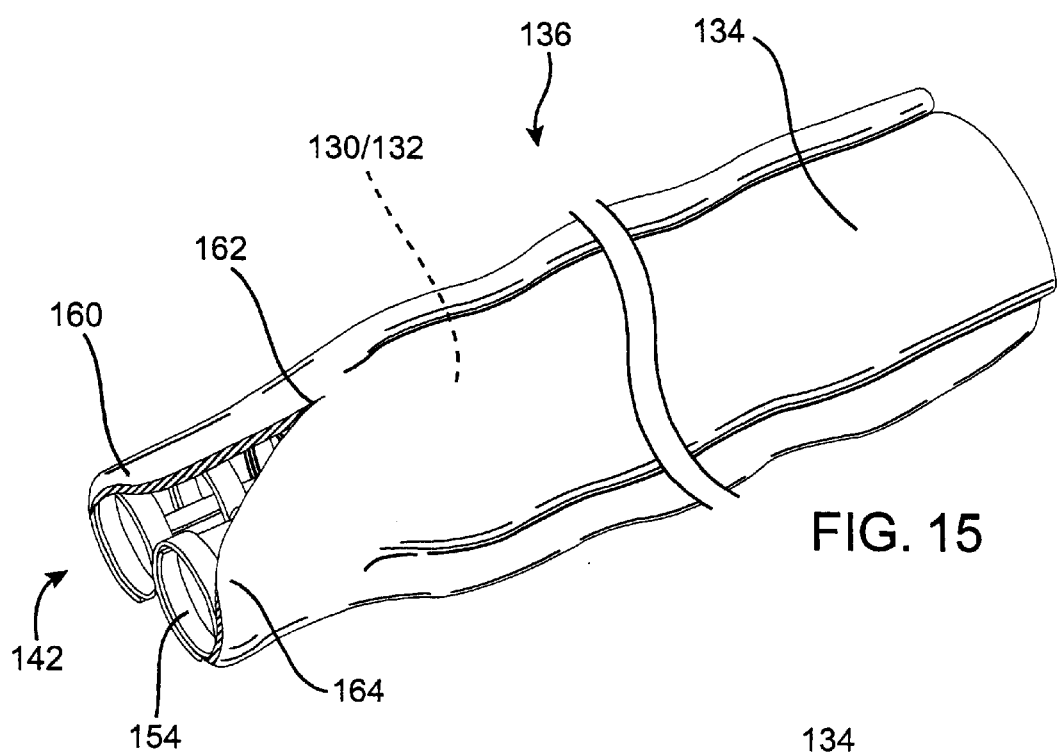
FIG. 15 is a perspective view of the vessel coupling shown in FIG. 13 coupled to a graft vessel adapted to be anastomosed to a target vessel, wherein the vessel coupling and the graft vessel are in a collapsed orientation.

FIG. 15 illustrates the stent 132 and the graft vessel 134 which comprise the stent-graft assembly 136 in their collapsed, or low profile orientation. The graft vessel 134 may be secured to the stent 132 by any suitable means (not shown), such as suture, adhesive, clips or fasteners, etc., and may comprise tissue, synthetic material, or a combination of the two, as explained above with respect to the previous embodiment. The graft vessel 134 is preferably folded somewhat to more closely approximate the diameter of the collapsed stent 132 and then retained in that condition.

Figure 16:
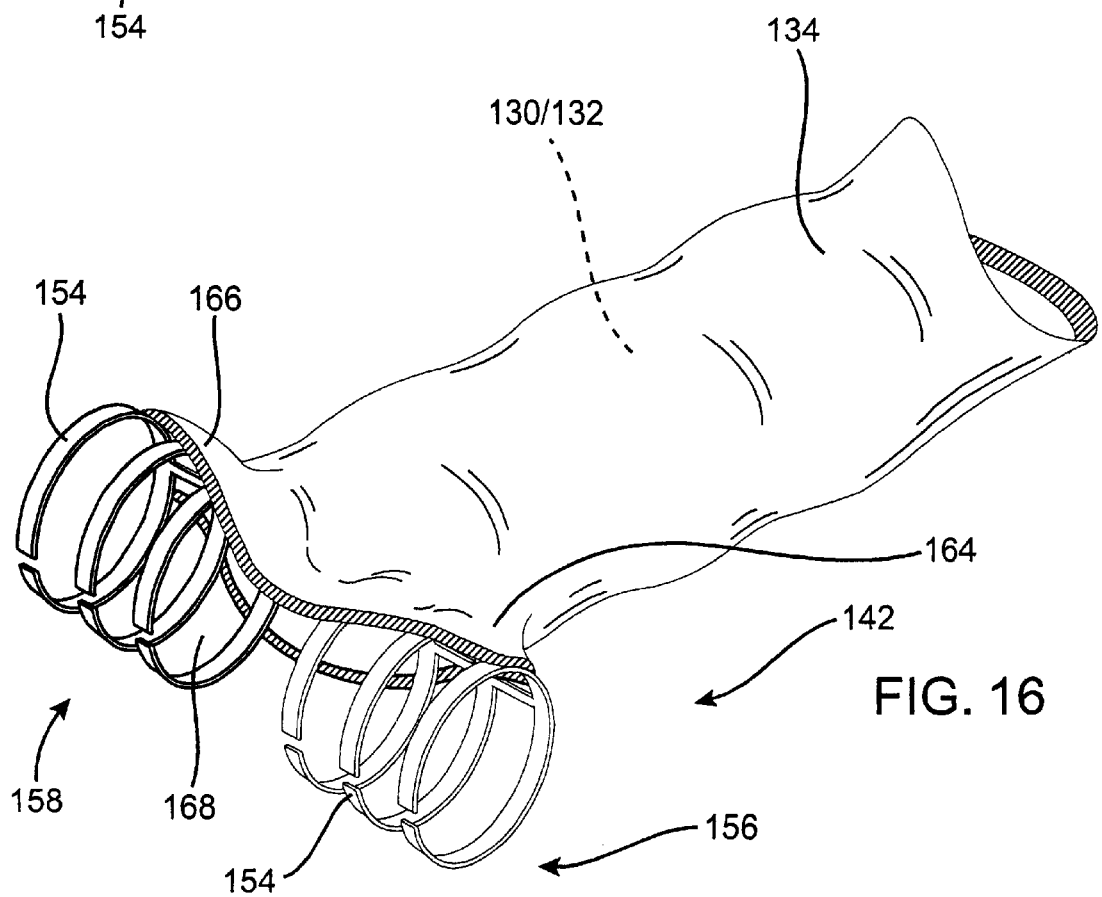
FIG. 16 is a perspective view illustrating the vessel coupling and the graft vessel shown in FIG. 15 in an expanded orientation.

The graft vessel 134 typically would be prepared for use in a CABG procedure by cutting the end of the vessel for anastomosis to the target vessel. In the illustrated embodiment the end 160 of the graft vessel 134 is splayed apart somewhat by a cut 162 to form leafs 164, 166 each of which overlies one of the sets 156, 158 of frame elements 154. The cut 162 permits the leafs 164, 166 to move apart as the frame 142 expands with the stent body 140. The resulting expanded orientation of the stent 132 and the graft vessel 134 is shown in FIG. 16. As can be seen the leafs 164, 166 partially surround the frame elements 154 with the lumen of the graft vessel aligned with the lumen of the stent 132 and in communication with a lumen 168 defined through the frame 142. As can be seen, flow through the lumen 168 in the direction of the arrows in FIG. 16 is not impeded by the graft vessel 134.

Figure 17:
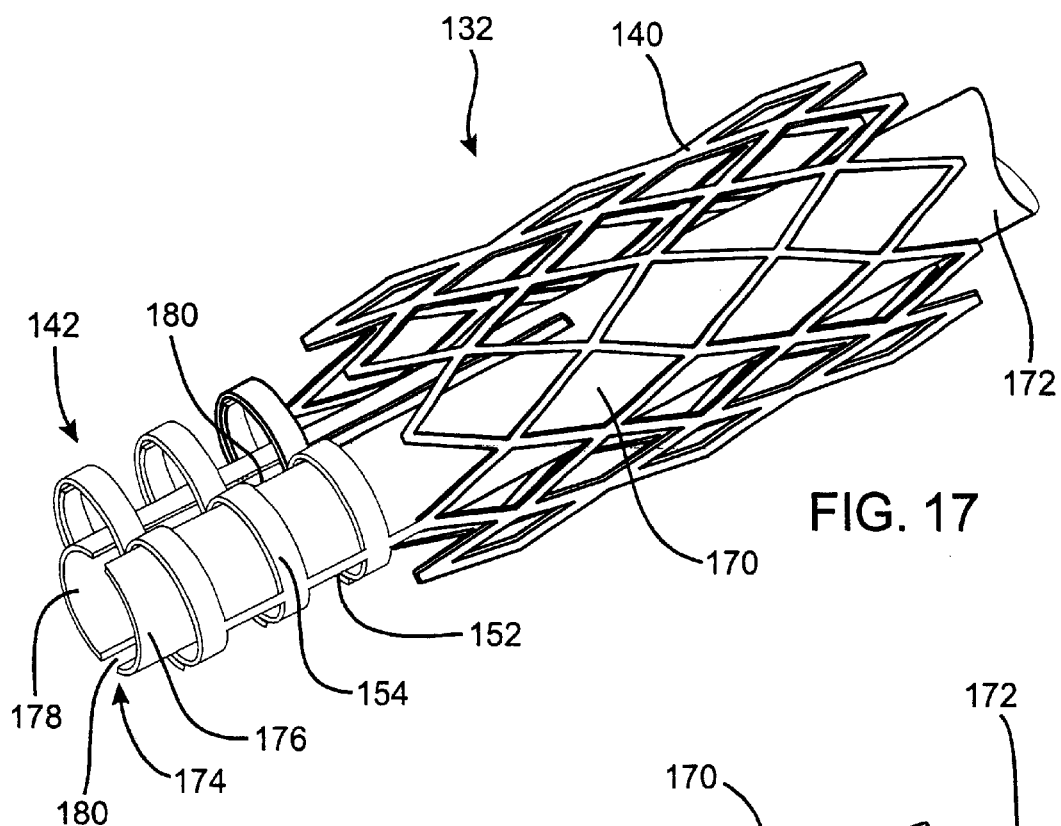
FIG. 17 is a perspective view of the vessel coupling shown in FIG. 13 loaded on a portion of an anastomosis device constructed according to the invention.
Figure 18:
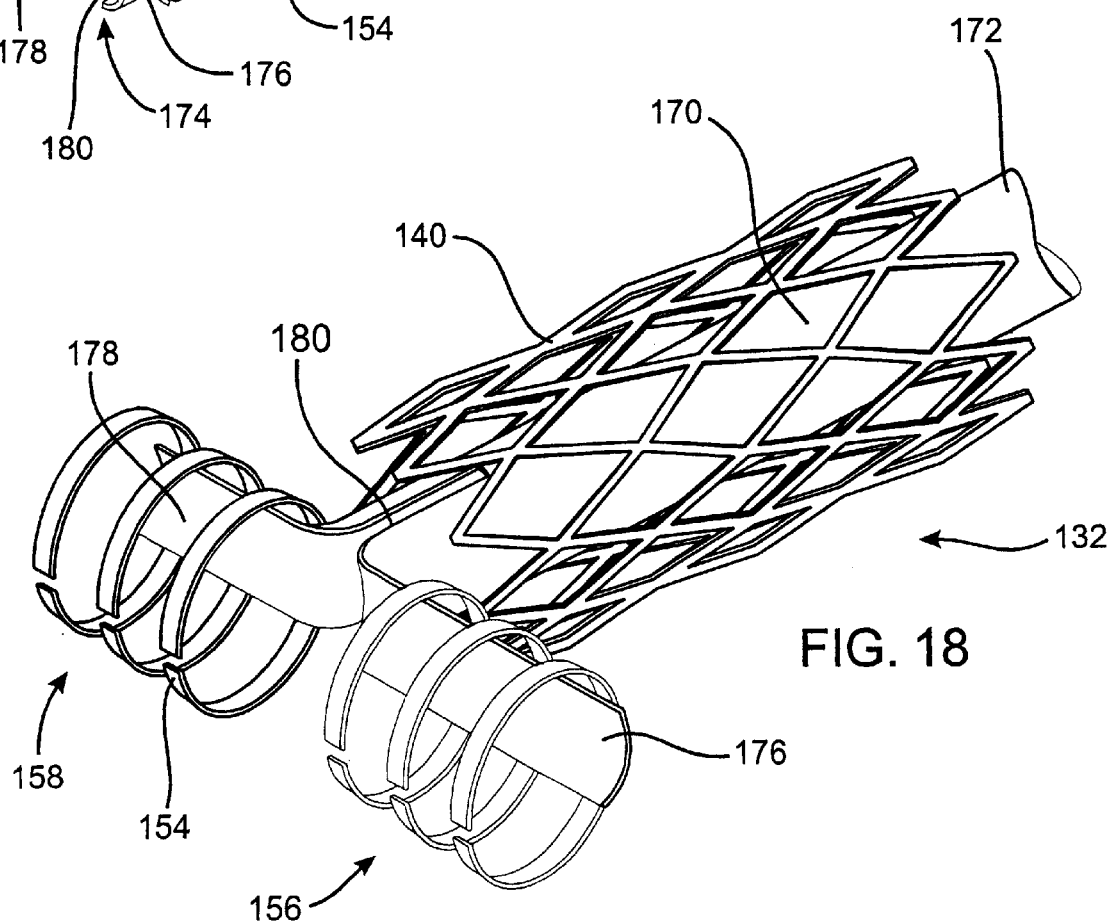
FIG. 18 is a perspective view of the vessel coupling shown in FIG. 17 after the anastomosis device has been actuated to expand the vessel coupling.
Figures 19, 19A:
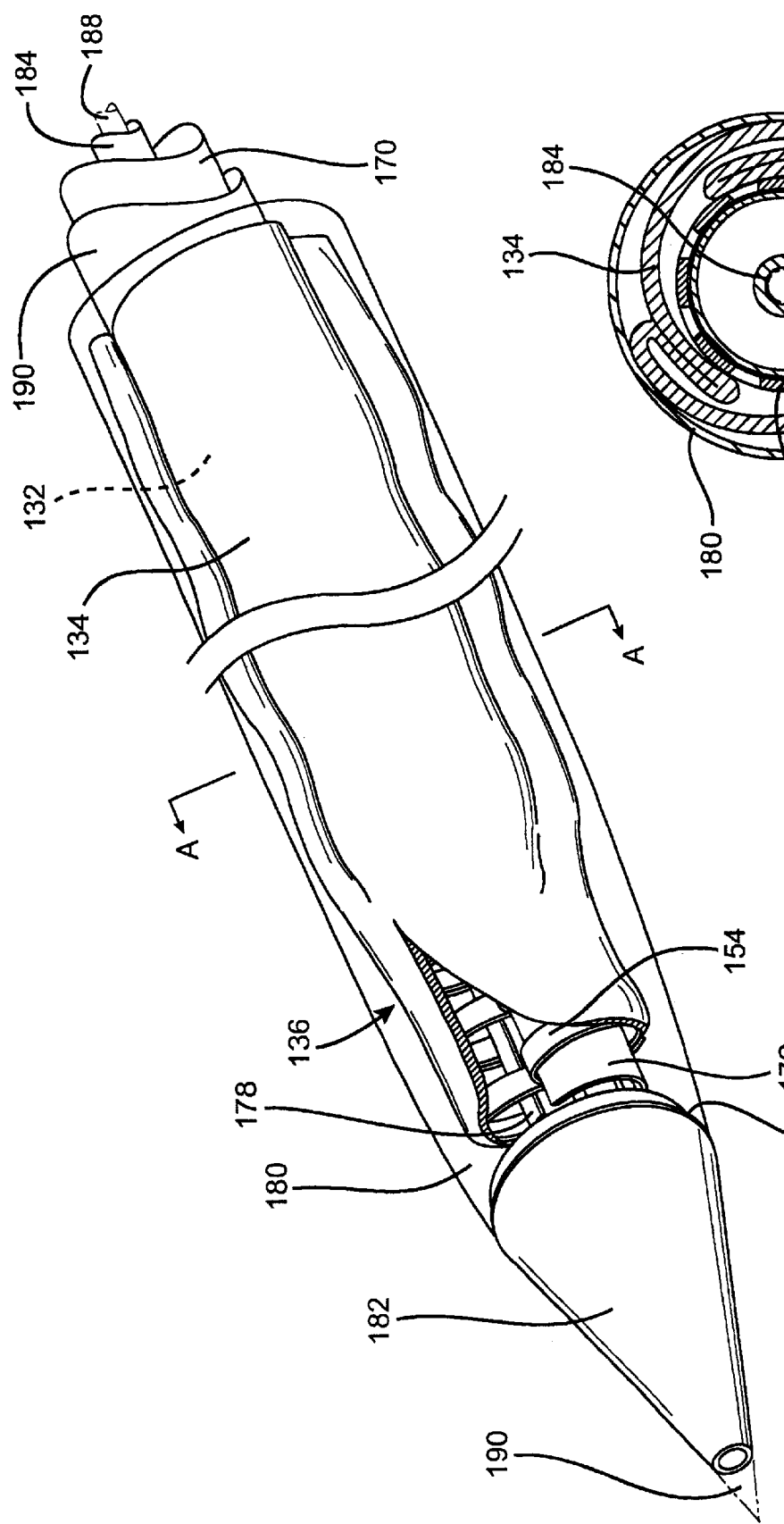
FIG. 19 is a perspective view of a portion of the anastomosis device partially shown in FIG. 17 loaded onto a delivery device.
FIG. 19A is a transverse sectional view of a portion of the anastomosis device taken along line A—A in FIG. 19.

FIGS. 17–18 depict the vessel coupling 130 in combination with a portion of an anastomosis device constructed according to the invention. The anastomosis device is designed to deliver a vessel coupling and graft vessel to a target vessel and create an anastomosis between the vessels, preferably while using no (or substantially no) suture. FIGS. 17–18 illustrate a guide member 170 which supports the stent body 140 and coupling frame 142, and also guides the frame elements 154 to their expanded orientation as they are uncovered by a sheath or cover (FIG. 19). The guide member 170 may be in the form of a hollow tube having a proximal end 172 and a distal end 174. The distal end 174 of the guide member 170 is split into first and second guide arms 176, 178 by slots 180 cut in the tube. The slots 180 result in the two guide arms 176, 1;78 comprising curved sections of the tube.

Referring to FIG. 17, the collapsed stent 132 is disposed over the guide member 170 with the coupling frame 142 located at the distal end 174 of the guide member. The graft vessel (not shown in FIGS. 17–18) may be attached to the stent 132 before the stent has been collapsed or crushed onto the guide member 170 or, alternatively, after the stent 132 has been collapsed onto the guide member. The frame elements 154 pass through the slots 180 and wrap around the guide arms 176, 178 (FIG. 17). If the stent is self-expanding, a sheath or cover is positioned over the device as explained above.

The guide member 170, and in particular the guide arms 176, 178, are preferably formed of a shape memory alloy that has been shape set to, the orientation shown in FIG. 18, which corresponds to the expanded orientation of the stent 132. Other materials such as stainless steel, titanium, polymers, etc., may be used to form the guide arms 176, 178 and/or the remainder of the guide member 170. In use, the guide arms 176, 178 are extended into the lumen of the target vessel ahead of the stent frame 142 and flare outwardly to move from the position shown in FIG. 17 to the unbiased position shown in FIG. 18. The stent 132 is then moved in a distal direction (from within the sheath) which results in the stent body 140 and the frame element sets 156, 158 to move to their expanded orientation. As this takes place the frame elements 154 ride over the guide arms 176, 178 to ensure the elements are positioned properly in, the target vessel.

Figure 20:
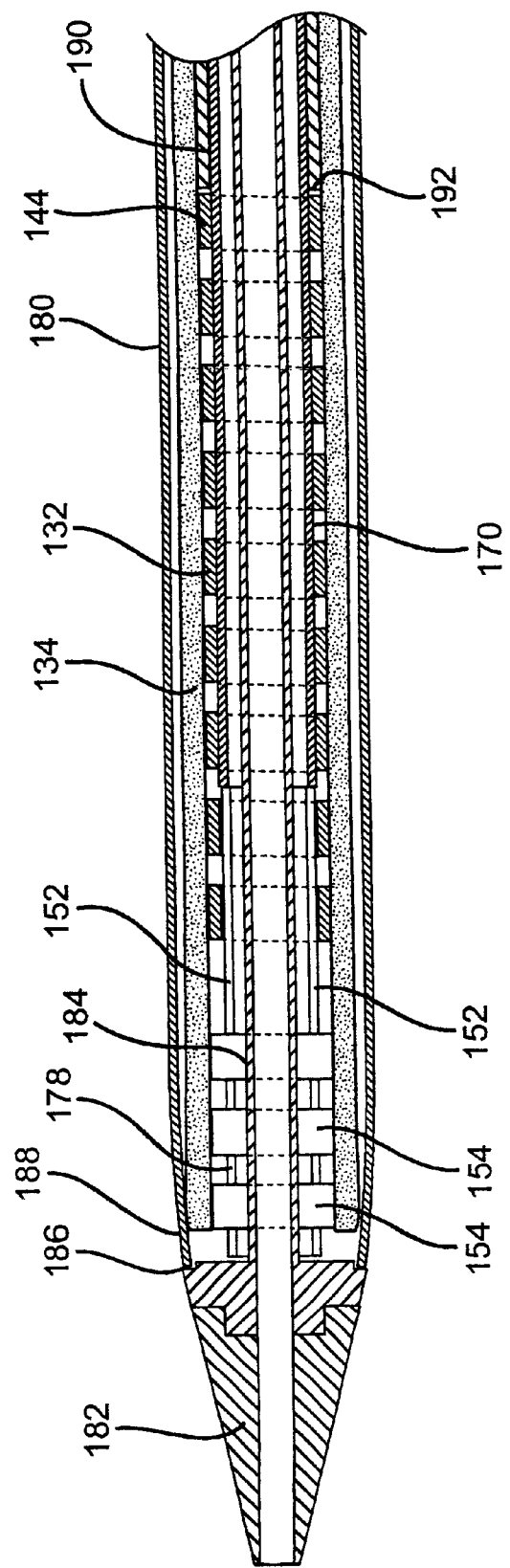
FIG. 20 is a longitudinal sectional view of a portion of the anastomosis device shown in FIG. 19.

FIGS. 19, 19A and 20 depict an anastomosis device including a stent-graft assembly 136 constructed as described above. FIG. 19 shows the distal portion of the device including the stent 132 and graft vessel 134 of the assembly 136 positioned over the guide member 170. A sheath 180 is disposed over the device and retains the stent-graft assembly 136 in its collapsed orientation for introduction into a target vessel. A nose cone dilator 182 is disposed at the distal end of the device and is used dilate an opening in tissue to introduce the device into a vessel lumen. The nose cone dilator 182 is supported by a shaft 184 extending through the bore in the guide member 170. The shaft 184 may extend through the device without contacting the various components; however, due to the resilient, and preferably superelastic characteristics of the guide arms 176, 178, the shaft 184 can be forced through the bore of the guide member 170.

FIG. 20 is a sectional view of the device shown in FIGS. 19–19A including a proximal portion of the device that includes mechanisms for actuating the guide member 170 and forcing the stent 132 out of the sheath 180. The nose cone dilator 182 is preferably formed with an external step 186 which receives the distal end 188 of the sheath. The sheath 180, which may be formed of the same materials described above with respect to the sheath in the previous embodiment, is preferably configured to mate with the nose cone dilator 182 and form a smooth transition to aid in dilating tissue. The nose cone dilator 182 may be passed through a preformed opening in the wall of the target vessel or, the nose cone dilator 182 may have a sharpened tip to pierce the wall of the vessel. Alternatively, the nose cone dilator shaft 184 may be hollow for passing the device over a guide wire or guide catheter previously introduced into the vessel. As still another alternative, the device may be used with an incising assembly (such as the assembly 16 described above regarding the previous embodiments) having an element configured to incise the wall of the vessel.

Referring to FIG. 20, the proximal portion of the device preferably includes one or more actuators for controlling movement of the guide member 170 and the stent-graft assembly 136 relative to the remainder of the device. A first actuator (not shown) is coupled to a proximal portion of the guide member 170 and is used to move the guide member distally from within the stent-graft assembly 136 and the sheath 180. A second actuator 190 (partially shown in FIG. 20) is disposed over the shaft 1:84 and the guide member 170 and has an end 192 that abuts (or is detachably coupled to) the proximal portion of the stent 132. The actuator 192 is used to move the stent 132 and graft vessel 134 distally to place the stent frame 142 within the lumen of the target vessel. It will be appreciated that any suitable actuator mechanism may be used.

Figure 21A:
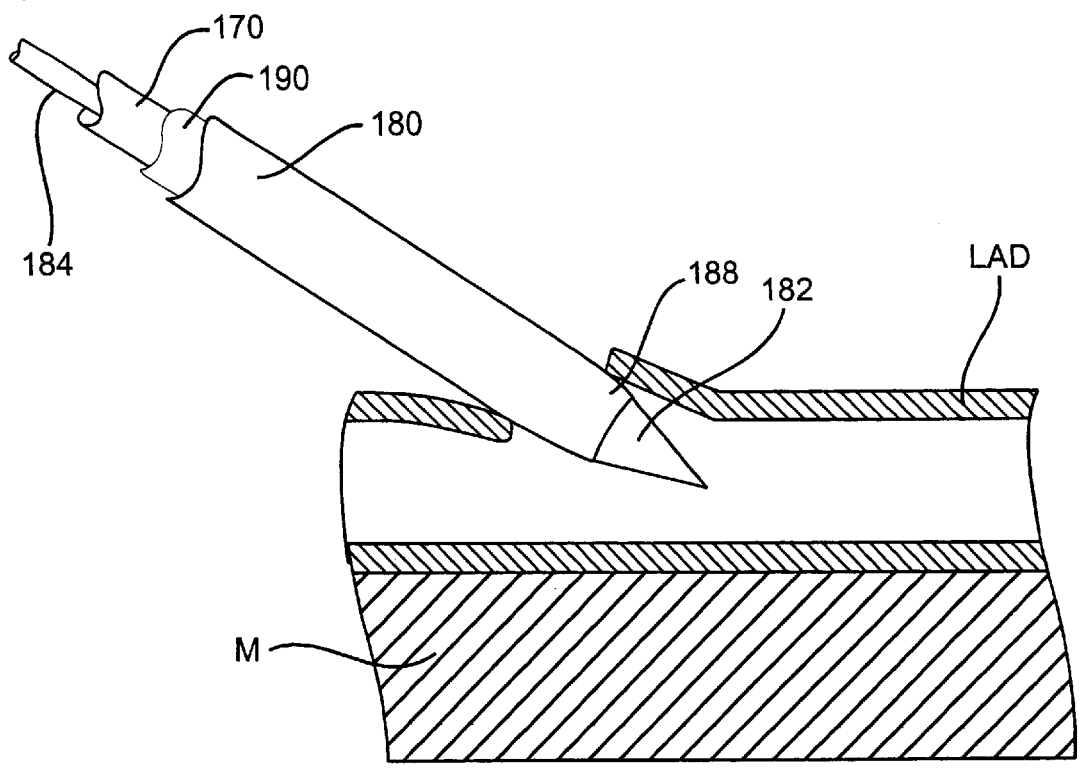
FIG. 21A is an enlarged sectional view of a portion of a heart including a coronary artery containing an obstruction, wherein the distal end of the anastomosis device shown in FIGS. 19–20 is positioned in the lumen of the coronary artery.

Turning now to FIGS. 21A–21I and 22, an exemplary application of the anastomosis device shown in FIGS. 13–20 will be described. FIG. 21A is an enlarged sectional view of a portion of a heart including the LAD and the heart wall M. The LAD contains an obstruction (not shown) located proximal to the site at which the device is introduced. It will be appreciated that the LAD shown in the Figures is only one example of a vessel that may be treated using the devices and methods of the invention. The distal end of the anastomosis device including the nose cone dilator 182 and the distal end 188 of the sheath 180 is shown introduced into the lumen of the LAD, which may be achieved using the incising assembly described above by placing the incising element 188 in the bore of the support shaft 184 with the sharpened tip 190 exposed (as: shown in phantom in FIG. 19). Alternatively, the nose cone dilator 182 may be formed with a sharpened tip used to pierce the vessel wall; another alternative is forming a surgical cut-down in the vessel wall.

Figure 21B:
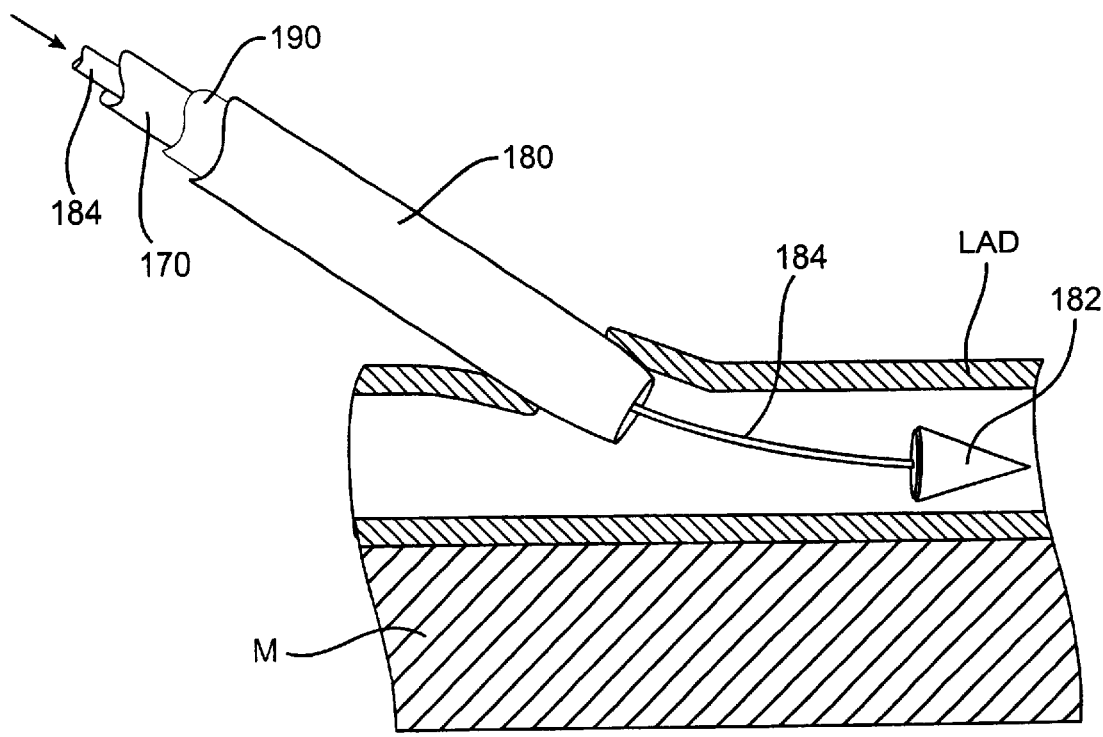
FIG. 21B is an enlarged sectional view of the portion of the heart shown in FIG. 21A illustrating the device being used to move a nose cone dilator downstream in the artery.

FIG. 21B shows the nose cone shaft 184 being extended from the distal end 188 of the sheath 180 to move the nose cone dilator 182 to an out-of- the-way position, for example, in a downstream direction within the lumen of the LAD. An actuator (not shown) may be used to push the nose cone dilator 182 out of the sheath 180 a distance sufficient to permit the vessel coupling 130, and in particular the coupling frame 142, to be deployed in the LAD. The nose cone dilator shaft 184 is preferably formed of a resilient material that provides sufficient column strength to push the nose cone dilator 182 distally while flexing as the device is moved from an introducing position (FIG. 21A) to a deploying position (FIG. 21C).

Figure 21C:
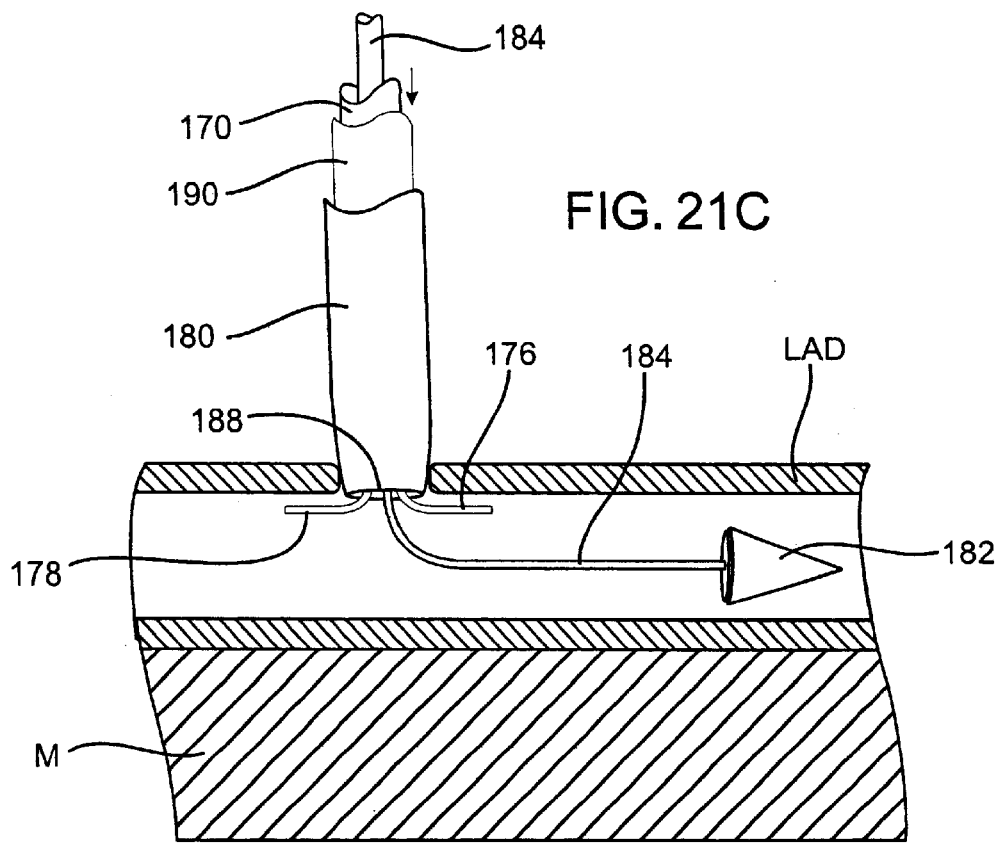
FIG. 21C is an enlarged sectional view of the portion of the heart shown in FIG. 21B illustrating the device in a desired orientation with vessel coupling guide arms partially deployed.

FIG. 21C shows the anastomosis device after it has been moved to a vessel coupling deploying position with respect to the LAD. With the device preferably positioned generally perpendicularly to the wall of the LAD, the guide arms 176, 178 of guide member 170 are extended from the distal end 188 of the sheath into the lumen of the LAD. The guide arms 176, 178 are formed to assume the position shown in FIG. 18 when released from within the sheath 180 and the stent 132. FIG. 21C shows the guide arms 176, 178 after they have been partially moved out of the sheath, 180.

Figure 21D:
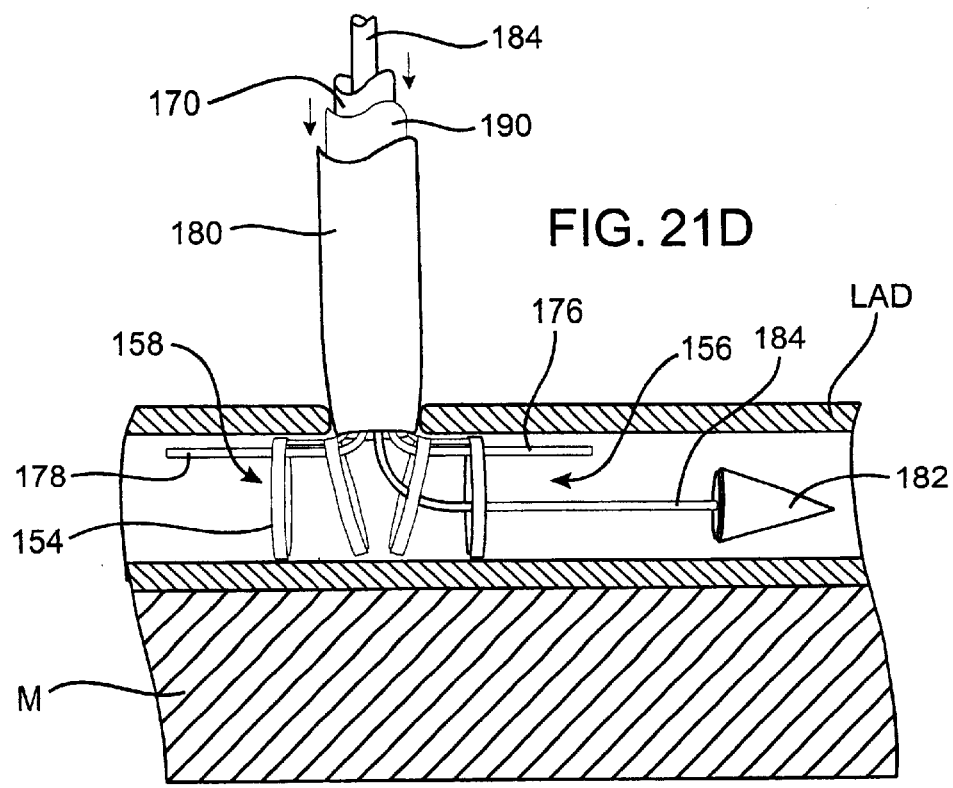
FIG. 21D is an enlarged sectional view of the portion of the heart shown in FIG. 21C illustrating the vessel coupling guide arms fully deployed with the vessel coupling being moved along the guide arms.

FIG. 21D shows the guide arms 176, 178 fully extended from the sheath 180 with the sets 156, 158 of frame elements 154 partially moved out of the sheath. As shown, the frame elements 154 ride along the guide arms 176, 178 which ensures the elements assume the desired orientation within the lumen of the LAD. It should be recognized that the invention may be carried out by using a different-or no guide member(s) for the vessel coupling.

Figure 21E:
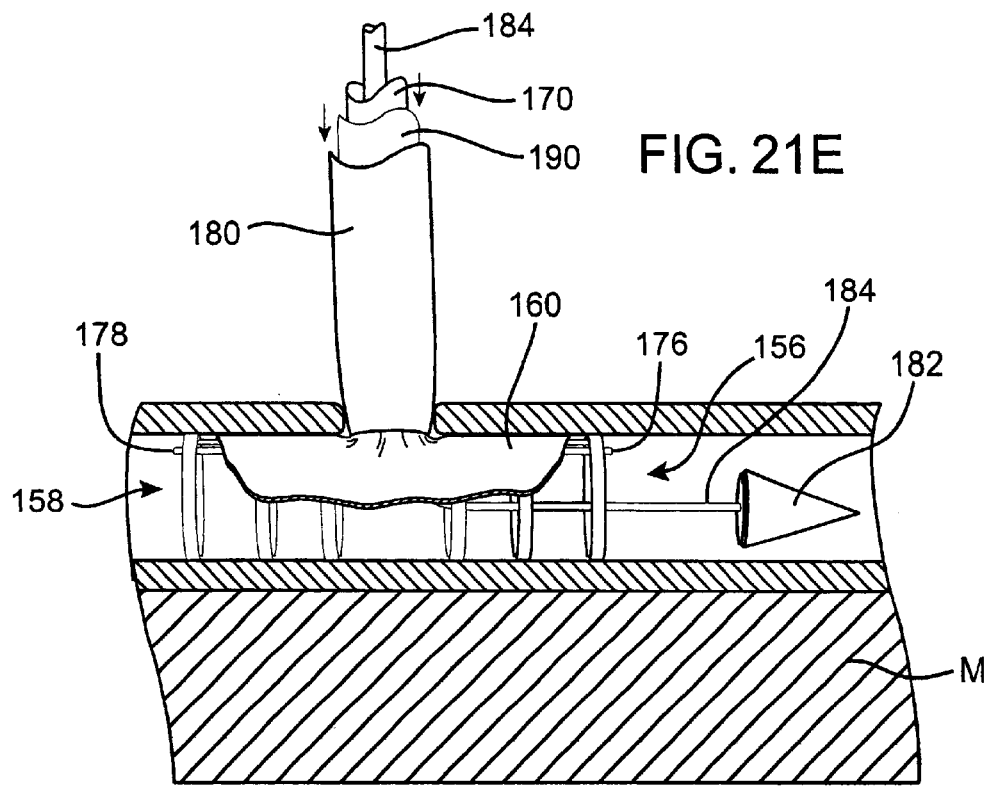
FIG. 21E is an enlarged sectional view of the portion of the heart shown in FIG. 21D illustrating the vessel coupling after it has been moved over the guide arms into the lumen of the coronary artery.

FIG. 21E shows the frame elements 154 of the vessel coupling 130 fully extended to their expanded orientation after the distal end 160 of the graft vessel 134 has moved into the lumen over the coupling frame 142. The frame elements 154 are configured to force the end 160 of the graft vessel 134 against the interior of the vessel. Thus, as seen in FIG. 21E, deploying the coupling frame 142 sandwiches the end 160 of the graft vessel 134 between the frame elements 154 and the interior of the vessel wall. This provides a tight seal at the junction of the LAD and the graft vessel 134 to prevent blood leakage. Forcing the tissue of the vessel end against the interior of the wall also minimizes the material in the lumen of the LAD to reduce the likelihood of thrombosis.

Figure 21F:
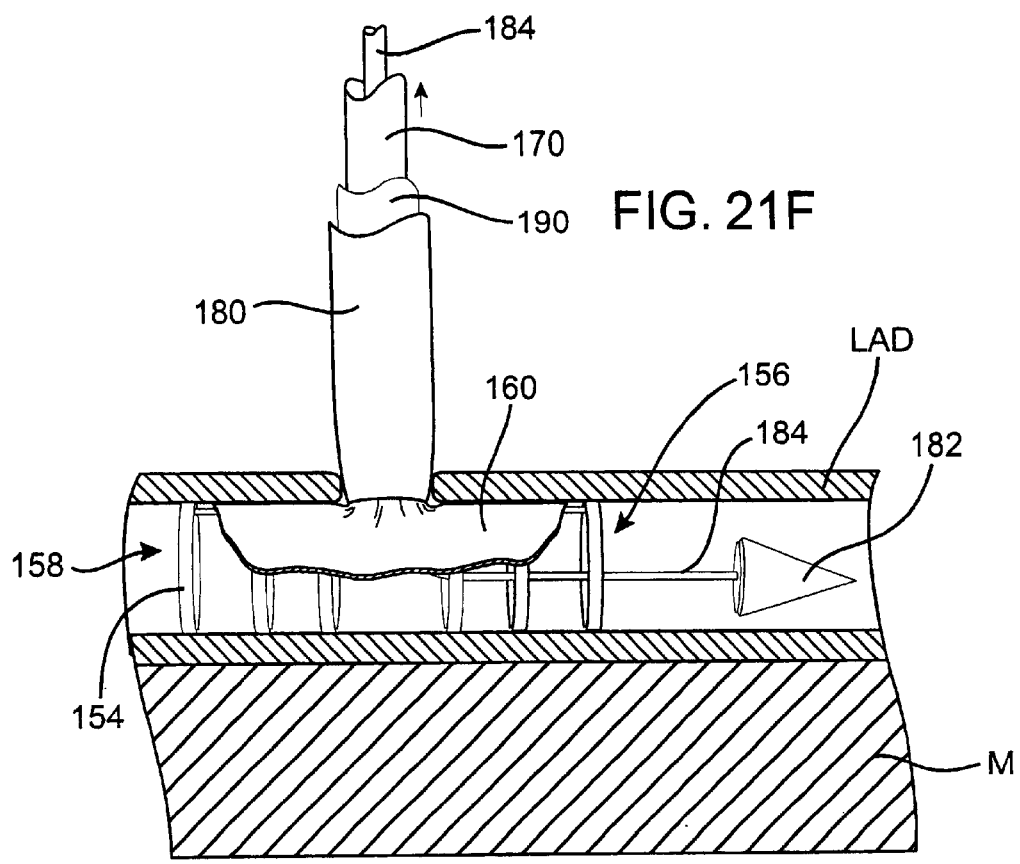
FIG. 21F is an enlarged sectional view of the portion of the heart shown in FIG. 21E illustrating the vessel coupling after the guide arms have been removed from the lumen of the coronary artery.
Figure 21G:
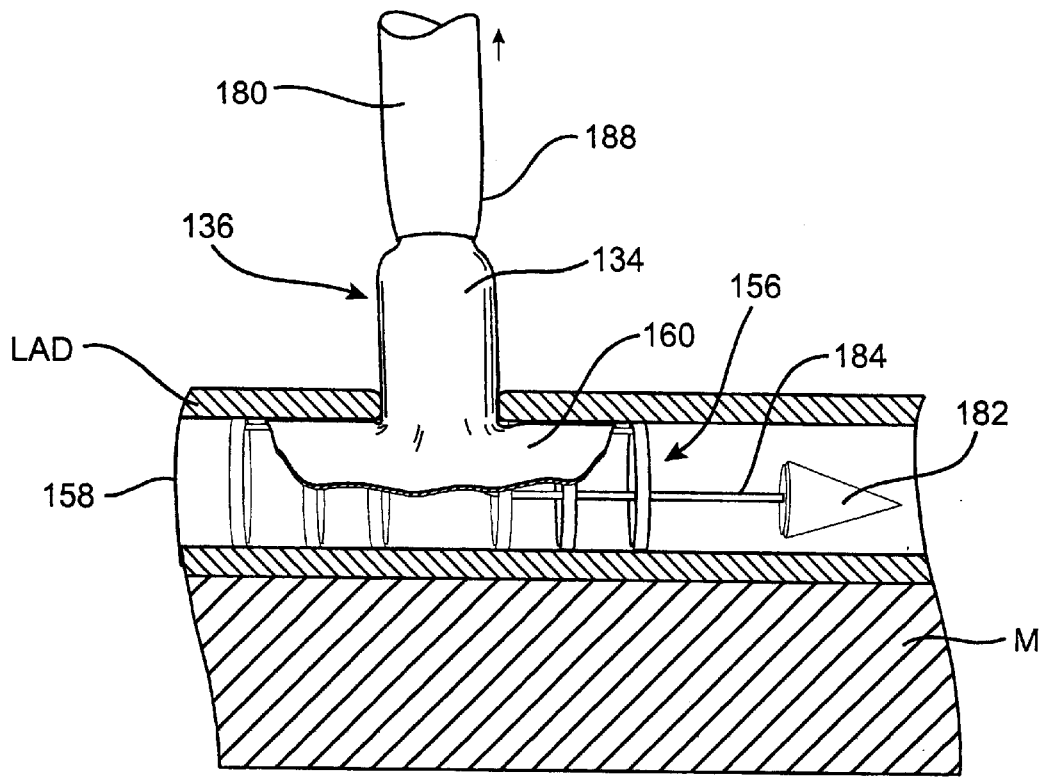
FIG. 21G is an enlarged sectional view of the portion of the heart shown in FIG. 21F illustrating a sheath being removed from the vessel coupling and the graft vessel to allow the coupling to expand.
Figure 21H:
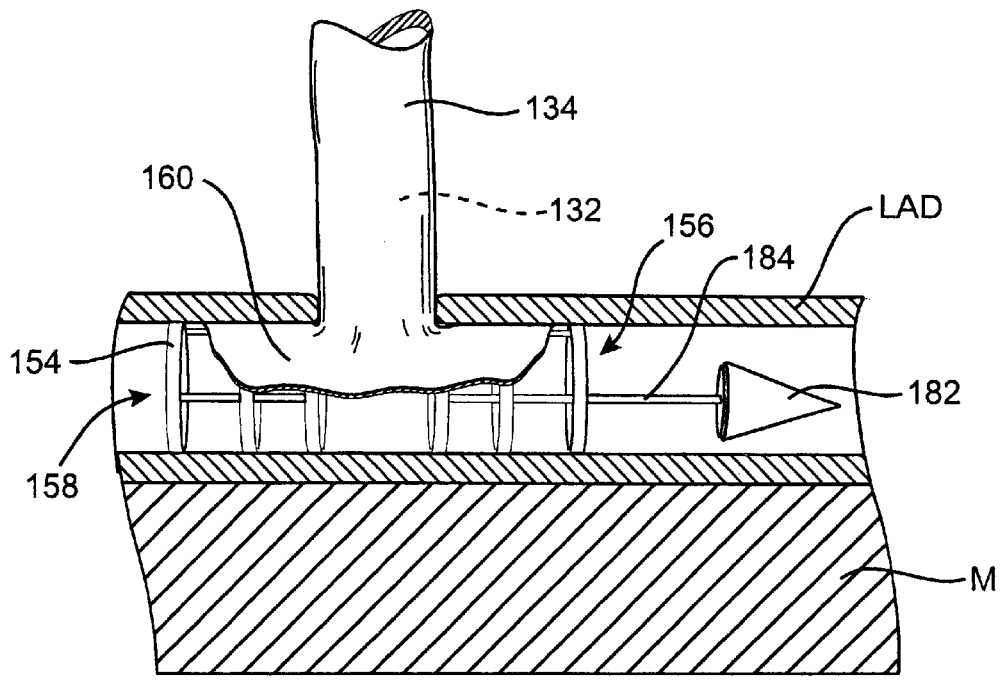
FIG. 21H is an enlarged sectional view of the portion of the heart shown in FIG. 21G illustrating the vessel coupling and the graft vessel in their fully expanded orientation.
Figure 21I:
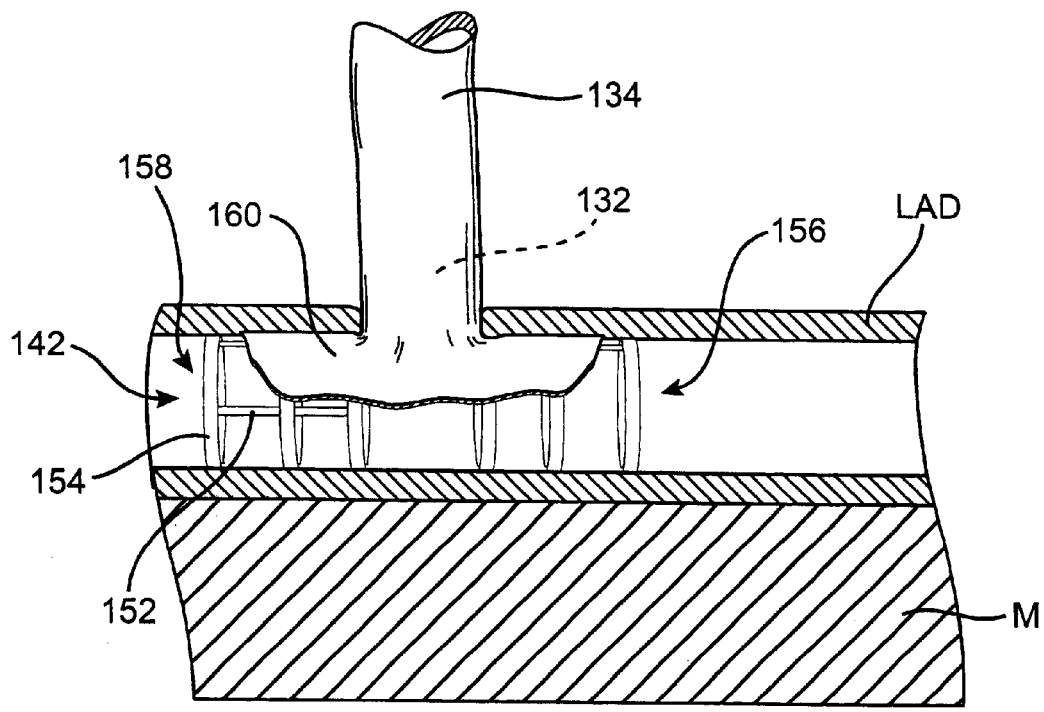
FIG. 21I is an enlarged sectional view of the portion of the heart shown in FIG. 21H after the device has been removed.
Figure 22:
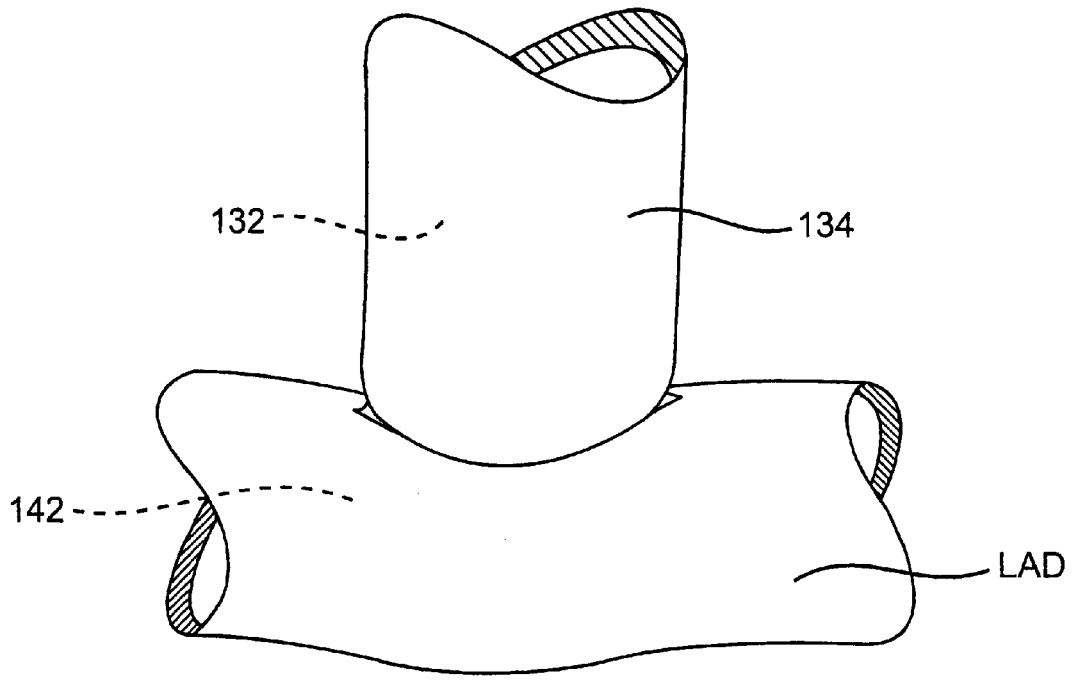
FIG. 22 is a schematic perspective view of the exterior of the portion of the heart shown in FIG. 21I illustrating the completed distal anastomosis.
Figure 23:
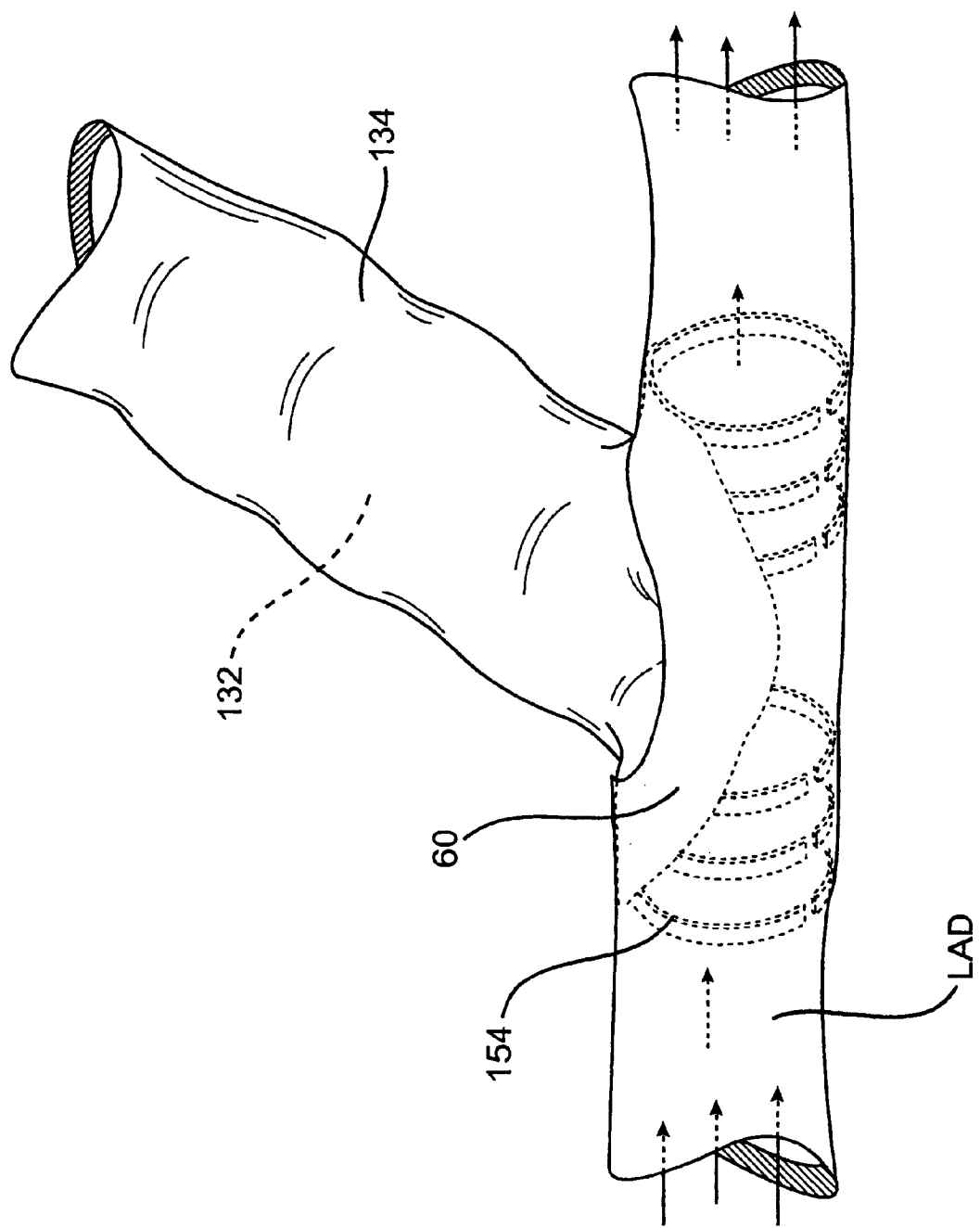
FIG. 23 is a schematic perspective view of the exterior of a portion of a patient's heart illustrating the manner in which an exemplary anastomosis formed according to the invention preserves native blood flow in the target vessel.

FIG. 21F shows the guide arms 176, 178 being retracted from the lumen of the LAD, which leaves only the coupling frame 142 and the end 160 of the graft vessel in the vessel lumen. Next, as shown in FIG. 21G, the sheath 180 is retracted from the stent-graft assembly 136 which allows the stent 132 to assume it expanded orientation. The stent 132 expands and firmly engages the wall of the graft vessel 136 as well as the wall of the LAD to maintain the junction of the vessels open. The shaft 184 is then retracted to remove the nose cone dilator 182 from the lumen of the LAD. The nose cone dilator is sized so that it can be passed through the frame elements 154 and the distal end 146 of the stent body 140. FIG. 21I shows the resulting configuration of the distal anastomosis. FIG. 22 shows the anastomosis as viewed from the exterior of the heart.

As can be seen from FIG. 21I, the anastomosis joining the graft vessel 134 and the LAD, in addition to providing a secure, leak tight connection, preserves native proximal flow in the LAD. Native proximal flow refers to any blood flowing from a proximal direction toward the anastomosis (from the left to the right in the Figures). This embodiment of the invention preserves native proximal flow because blood is free to flow past the coupling frame 142. This is highly desirable because it avoids creating a dead space in the lumen of the LAD which would result in inadequate or no blood flow for a portion of the myocardium. Thus, whereas the anastomosis formed by the previous embodiments of the invention may restrict or block native blood flow in the target vessel, this embodiment forms an anastomosis that does not block such flow.

Those in the art will recognize many possible variations of the invention as described and illustrated herein. For instance, a rigid or non-expandable vessel coupling may be used to create the anastomosis. The coupling may comprise a rigid tube that is coupled to the graft vessel by suitable means and is configured to be placed in the target vessel. For example, the conduit could be oversized with respect to the target vessel and the vessel dilated up to receive the conduit. The target vessel would then close back down around the conduit to securely hold the components together without using suture.

Similarly, it will be appreciated that a vessel coupling configured to preserve native blood flow in a target vessel may be constructed differently than that shown. For example, the portion of the vessel coupling that is disposed in the target vessel could take the form of a conventional coronary stent joined to the portion of the coupling disposed in the graft vessel. Further, the portion of the vessel coupling that permits native flow through the target vessel could control or meter the flow. Other variations may of course be used as well.

It will be appreciated that the features of the various preferred embodiments described herein may be used together or separately, while the illustrated methods and devices may be modified or combined in whole or in part. As an example, the anastomosis formed between the graft and target vessels may be suture-free while allowing or blocking native flow through the target vessel; alternatively, the anastomosis may be formed to allow native flow through the target vessel but be created using to some extent conventional suturing techniques.

Further, it will be understood that the embodiments may be used in various types of procedures, for example, the surgical approach depicted in the Figures, an open surgical procedure including a median sternotomy, or a minimally invasive procedure utilizing one or more relatively small access openings or ports. Endoscopes or thoracoscopes may be used for visualization if the procedure is truly minimally invasive. Similarly, the different embodiments may be used in beating heart procedures, stopped-heart procedures utilizing cardiopulmonary bypass (CPB), or procedures during which the heart is intermittently stopped and started. Finally, any suitable delivery device, instrument or catheter may be used in conjunction with the invention.

The preferred embodiments of the invention are described above in detail for the purpose of setting forth a complete disclosure and for sake of explanation and clarity. It will be readily understood that the scope of the invention defined by the appended claims will encompass numerous changes and modifications.

What is claimed is:

1. A method for forming an anastomosis between a first vessel and a second vessel, the method comprising steps of:

providing a vessel coupling having a main leg, a first leg and a second leg, the main leg having a proximal opening and a distal opening, the first and second legs being movable from a collapsed position to an expanded position, the; first and second legs extending distally from the distal opening of the main leg when in the collapsed position, the first and second legs extending radially from the main leg when in the expanded position so that the first and second legs and the main body together form a generally T-shaped connector;

attaching a first vessel to the main leg of the vessel coupling;

forming an opening in a second vessel having a lumen;

introducing the first and second legs into the second vessel through the opening, the first and second legs moving to the expanded position within the second vessel so that the first and second legs form the T-shaped connector thereby coupling the first and second vessels together.

2. The method of claim 1, wherein the providing step is carried out with the first and second legs being radially expandable.

3. The method of claim 1, wherein the providing step is carried out with the main leg being radially expandable.

4. The method of claim 1, wherein the providing step is carried out with the first and second legs forming rings.

5. method of claim 1, wherein the providing step is carried out with the main leg of the vessel coupling having a conduit; that is placed at least partially into the lumen of the first vessel.

6. The method of claim 5, wherein the providing step is carried out with the expandable conduit being a stent.

7. The method of claim 1, wherein the providing step is carried out with the first vessel comprising a combination of autologous tissue and synthetic graft material adapted to be anastomosed to a coronary artery.

8. The method of claim 1, wherein the attaching step is carried out with the vessel coupling being coupled to the first vessel so as to overlap a portion of the first vessel, and the introducing step is carried out to force the overlapped portion of the first vessel against the second vessel.

9. The method of claim 1, wherein the providing step is carried out with the first vessel being a saphenous vein graft having a, first end attached to the vessel coupling and a second end anastomosed to the patient's aorta to complete a coronary bypass procedure.

10. The method of claim 1, further comprising the step of providing a sheath over the vessel coupling and at least a portion of the first vessel.

11. The method of claim 1, wherein the providing step is carried out with the first vessel having an autologous graft coupled to a graft formed of ePTFE, and the second vessel is a coronary artery.

* * * * *